(12) United States Patent
Lin et al.

(10) Patent No.: US 11,504,422 B2
(45) Date of Patent: *Nov. 22, 2022

(54) BIODEGRADABLE NANOCOMPLEX

(71) Applicant: NATIONAL CHENG KUNG UNIVERSITY, Tainan (TW)

(72) Inventors: Yee-Shin Lin, Tainan (TW); Yu-Hung Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 504 days.

This patent is subject to a terminal disclaimer.

(21) Appl. No.: 15/242,626

(22) Filed: Aug. 22, 2016

(65) Prior Publication Data

US 2017/0043007 A1 Feb. 16, 2017

Related U.S. Application Data

(63) Continuation-in-part of application No. 13/923,699, filed on Jun. 21, 2013, now abandoned.

(30) Foreign Application Priority Data

Jan. 9, 2013 (TW) .................................. 102100788

(51) Int. Cl.

| A61K 47/34 | (2017.01) |
| A61K 47/36 | (2006.01) |
| A61K 39/00 | (2006.01) |
| A61K 39/12 | (2006.01) |
| C12N 7/00 | (2006.01) |
| A61K 39/385 | (2006.01) |
| B82Y 5/00 | (2011.01) |

(52) U.S. Cl.
CPC ............ *A61K 39/12* (2013.01); *A61K 39/385* (2013.01); *C12N 7/00* (2013.01); *A61K 47/34* (2013.01); *A61K 47/36* (2013.01); *A61K 2039/55555* (2013.01); *A61K 2039/55583* (2013.01); *A61K 2039/575* (2013.01); *A61K 2039/6087* (2013.01); *A61K 2039/6093* (2013.01); *B82Y 5/00* (2013.01); *C12N 2770/24134* (2013.01)

(58) Field of Classification Search
CPC ................... A61K 47/34; A61K 47/36; A61K 2039/55555; A61K 2039/44483; A61K 2039/6087; A61K 2039/609
See application file for complete search history.

(56) References Cited

U.S. PATENT DOCUMENTS

| 7,993,625 | B1 | 8/2011 | Sung et al. | |
| 10,052,390 | B2 * | 8/2018 | Lin .................. | A61K 39/12 |
| 2006/0147539 | A1 | 7/2006 | Sung et al. | |
| 2007/0116771 | A1 * | 5/2007 | Sung .................. | A61K 9/0019 |
| | | | | 424/489 |

FOREIGN PATENT DOCUMENTS

| CN | 101360486 A | 2/2009 |
| CN | 101374530 A | 2/2009 |
| EP | 2428221 A1 | 3/2012 |
| TW | 201210614 A | 3/2012 |

OTHER PUBLICATIONS

Lin et al., Biomacromolecules, 8, pp. 146-152. (Year: 2007).*
Antunes et al., Biomacromolecules, 12, pp. 4183-4195. (Year: 2011).*
Chinese Office Action dated Aug. 18, 2015 in Chinese Application No. 201310308965.2, a foreign corresponding application of U.S. Appl. No. 13/923,699, 14 pages. Translated.
European Search Report and Written Opinion dated Dec. 17, 2013 in European Application No. 13177243.6, a foreign corresponding application of U.S. Appl. No. 13/923,699, 6 pages.
Lin, Gengping "Development of Topical Delivery System for Minoxidil," 2003. Thesis, Department of Medicine and Hygiene, Taipei Medical University, Taiwan. Abstract.
Lin et al., "Preparation of Nanoparticles Composed of Chitosan/Poly-gamma-glutamic Acid and Evaluation of Their Permeability through Caco-2 Cells," Biomacromolecules 2005, 6, 1104-1112.
Nada et al., "Development of novel formulations to enhance in vivo transdermal permeation of tocopherol," Sep. 2014. Acta Pharmaceutica, 64(3): 299-309.
Taiwanese Office Action dated Mar. 1, 2017 in Taiwanese Application No. 10620229100, a foreign corresponding application of U.S. Appl. No. 13/923,699, 12 pages. Translated.
Wang et al., "Preparation and Properties of the gamma-Poly Glutamic acid/Chitosan Load Paclitaxel Composite Nanoparticles," Guangzhou Chemical Industry, vol. 40 No. 16 Aug. 2012.

* cited by examiner

*Primary Examiner* — Abigail Vanhorn
(74) *Attorney, Agent, or Firm* — Lee & Hayes, P.C.

(57) ABSTRACT

The present invention relates to a biodegradable nanocomplex. The biodegradable nanocomplex comprises a first electrically charged substance, a charge-redistribution substance, a second electrically charged substance and a carried substance, for holding the carried substance inside. The first electrically charged substance and the carried substance have the same electrical polarity, and the biodegradable nanocomplex has a nonuniformly and positively charge distribution along a radial direction thereof. The nonuniformally and positively charge distribution comprises a first electrically charged portion having substantially electrical neutrality, a second electrically charged portion surrounding the first electrically charged portion, and a third electrically charged portion surrounding the second electrically charged portion, in which the third electrically charged portion comprises an outermost surface of the biodegradable nanocomplex, thereby modulating the carried substance towards the desired immune responses via the nonuniformly and positively charge distribution.

10 Claims, 23 Drawing Sheets
(10 of 23 Drawing Sheet(s) Filed in Color)
Specification includes a Sequence Listing.

SEQUENCE LISTING

<160> NUMBER OF SEQ ID NOS: 2

<210> SEQ ID NO 1
<211> LENGTH: 352
<212> TYPE: PRT
<213> ORGANISM: Artificial sequence
<220> FEATURE:
<223> OTHER INFORMATION: Recombinant protein of Dengue virus NS1 and
      Japanese encephalitis virus NS1

<400> SEQUENCE: 1

```
Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
    50                  55                  60

Asn Leu Met Trp Lys Gln Ile Thr Pro Glu Leu Asn His Ile Leu Ser
65                  70                  75                  80

Glu Asn Glu Val Lys Leu Thr Ile Met Thr Gly Asp Ile Lys Gly Ile
                85                  90                  95

Met Gln Ala Gly Lys Arg Ser Leu Arg Pro Gln Pro Thr Glu Leu Lys
            100                 105                 110

Tyr Ser Trp Lys Thr Trp Gly Lys Ala Lys Met Leu Pro Thr Glu Ser
        115                 120                 125

His Asn Gln Thr Phe Leu Ile Asp Gly Pro Glu Thr Ala Glu Cys Pro
    130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Arg Glu Lys Gln Asp
                165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
        195                 200                 205

Thr Trp Lys Ile Glu Lys Ala Ser Phe Ile Glu Val Lys Ser Cys His
```

```
                210                 215                 220
Trp Pro Lys Pro His Thr Leu Trp Ser Asn Gly Val Leu Glu Ser Glu
225                 230                 235                 240

Met Ile Ile Pro Lys Asn Phe Ala Gly Pro Val Ser Gln His Asn Tyr
                245                 250                 255

Arg Pro Gly Tyr His Thr Gln Thr Ala Gly Pro Trp His Leu Gly Lys
                260                 265                 270

Leu Glu Met Asp Phe Asp Phe Cys Glu Gly Thr Thr Val Val Val Thr
                275                 280                 285

Glu Asp Cys Gly Asp Arg Gly Pro Ser Leu Arg Thr Thr Thr Ala Ser
290                 295                 300

Gly Lys Leu Ile Thr Glu Trp Cys Cys Arg Ser Cys Thr Leu Pro Pro
305                 310                 315                 320

Leu Arg Tyr Arg Gly Glu Asp Gly Cys Trp Tyr Gly Met Glu Ile Arg
                325                 330                 335

Pro Leu Lys Glu Lys Glu Glu Asn Leu Val Asn Ser Leu Val Thr Ala
                340                 345                 350

<210> SEQ ID NO 2
<211> LENGTH: 270
<212> TYPE: PRT
<213> ORGANISM: Artificial sequence
<220> FEATURE:
<223> OTHER INFORMATION: Recombinant protein of Dengue virus NS1

<400> SEQUENCE: 2

Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
                20                  25                  30

Lys Phe Gln Pro Glu Ser Pro Ser Lys Leu Ala Ser Ala Ile Gln Lys
            35                  40                  45

Ala His Glu Glu Gly Ile Cys Gly Ile Arg Ser Val Thr Arg Leu Glu
        50                  55                  60

Asn Leu Met Trp Lys Gln Ile Thr Pro Glu Leu Asn His Ile Leu Ser
65                  70                  75                  80

Glu Asn Glu Val Lys Leu Thr Ile Met Thr Gly Asp Ile Lys Gly Ile
                85                  90                  95

Met Gln Ala Gly Lys Arg Ser Leu Arg Pro Gln Pro Thr Glu Leu Lys
                100                 105                 110

Tyr Ser Trp Lys Thr Trp Gly Lys Ala Lys Met Leu Pro Thr Glu Ser
            115                 120                 125

His Asn Gln Thr Phe Leu Ile Asp Gly Pro Glu Thr Ala Glu Cys Pro
        130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Arg Glu Lys Gln Asp
                165                 170                 175

Val Phe Cys Asp Ser Lys Leu Met Ser Ala Ala Ile Lys Asp Asn Arg
                180                 185                 190

Ala Val His Ala Asp Met Gly Tyr Trp Ile Glu Ser Ala Leu Asn Asp
            195                 200                 205

Thr Trp Lys Ile Glu Lys Ala Ser Phe Ile Glu Val Lys Ser Cys His
        210                 215                 220

Trp Pro Lys Pro His Thr Leu Trp Ser Asn Gly Val Leu Glu Ser Glu
```

-continued

```
            225                 230                 235                 240

Met Ile Ile Pro Lys Asn Phe Ala Gly Pro Val Ser Gln His Asn Tyr
                245                 250                 255

Arg Pro Gly Tyr His Thr Gln Thr Ala Gly Pro Trp His Leu
                260                 265                 270
```

BIODEGRADABLE NANOCOMPLEX

RELATED APPLICATIONS

This application is a continuation-in-part of U.S. application Ser. No. 13/923,699, filed Jun. 21, 2013, which claims priority of Taiwan Application Serial Number 102100788, filed on Jan. 9, 2013, the entirety of which is incorporated by reference herein.

BACKGROUND OF THE INVENTION

Field of Invention

The present invention relates to a biodegradable nanocomplex. More particularly, the present invention relates to a biodegradable nanocomplex has a nonuniformally and positively charge distribution along a radial direction thereof for holding a carried substance inside.

Description of Related Art

Many researches reported that biomacromolecules can be used as drug carriers for delivering drugs. For example, liposome is used as a drug carrier in drug delivery system for many compounds, such as pharmaceutical active compound, diagnostic substance, and cosmetics. Up to now, the liposome is one of most potential drug carriers. The liposome is a tiny bubble with one-bilayer or multi-bilayer structure, which encapsulates a hydrophilic region inside a hydrophobic membrane so that a dissolved hydrophilic substance can be held in the liposome, and a hydrophobic substance can be dissolved into the membrane. The bilayer composition of the liposome is similar as that of organism's cell membrane and has biocompatibility and biodegradability, so the liposome is widely used as a drug carrier in drug delivery application. The liposome is mostly applied to the several human subject trial and cancer cell line test because the liposome can be fused into almost any organism structures. The liposome is applied to many human subject trials on many cancer diseases, acquired immune deficiency syndrome (AIDS), viral and bacterial infectious diseases, multiple myeloma, kaposi sarcoma, cryptococcosis meningitis and anti-fungal effect, and is applied to be as a carrier for erythropoietin and drugs delivery.

SUMMARY OF THE INVENTION

In view of the aforementioned disadvantages of the traditional macromolecular (drug, protein etc.,) carrier in actual implementation, an aspect of the present invention is to provide a biodegradable nanocomplex, which has a nonuniformally and positively charge distribution along a radial direction thereof, so as to hold a carried substance inside and to modulate the carried substance towards the desired immune responses via the nonuniformally and positively charge distribution.

Accordingly, the invention provides a biodegradable nanocomplex, which comprises a first electrically charged substance, a charge-redistribution substance, a second electrically charged substance and a carried substance, for holding the carried substance inside. The first electrically charged substance and the carried substance have the same electrical polarity, and the biodegradable nanocomplex has a nonuniformally and positively charge distribution along a radial direction thereof, and the nonuniformally and positively charge distribution comprises a first electrically charged portion having a first volume charge density, a second electrically charged portion surrounding the first electrically charged portion, and a third electrically charged portion surrounding the second electrically charged portion. In an example, the first volume charge density is substantially neutral. The third electrically charged portion comprises an outermost surface of the biodegradable nanocomplex.

According to an embodiment of the present invention, the carried substance and first electrically charged substance are negatively charged.

According to an embodiment of the present invention, the second electrically charged substance is positively charged.

According to an embodiment of the present invention, the charge-redistribution substance is negatively charged or positively charged.

According to an embodiment of the present invention, when the carried substance and first electrically charged substance are positively charged, the second electrically charged substance can be positively charged, and the charge-redistribution substance can be negatively charged or positively charged.

According to an embodiment of the present invention, the first electrically charged substance, the charge-redistribution substance and/or the second electrically charged substance are respectively selected from the group consisting of chitosan (CS), gelatin, cationic cyclodextrin, cationic dextran, poly(L-lysine), polyethylenimine (PEI) and polyamidoamine when the first electrically charged substance, the charge-redistribution substance and/or the second electrically charged substance are positively charged.

According to an embodiment of the present invention, the first electrically charged substance and/or the charge-redistribution substance are respectively selected from the group consisting of γ-polyglutamic acid (γ-PGA) and heparin when the first electrically charged substance and/or the charge-redistribution substance are negatively charged.

According to an embodiment of the present invention, the biodegradable nanocomplex has a zeta potential of 10 mV to 40 mV.

According to an embodiment of the present invention, a molar ratio of the charge-redistribution substance to the first electrically charged substance is 0.05 to 1.00.

With application to the biodegradable nanocomplex, a desired biodegradable nanocomplex with the nonuniformally and positively charge distribution can be easily produced, for saving the testing numbers, obtaining the biodegradable nanocomplex with more uniform diameter and less standard deviation, and providing better modulation of the carried substance towards the desired immune responses.

It is to be understood that both the aforementioned general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows. The patent or application file contains at least one drawing executed in color. Copies of this patent or patent application publication with color drawing(s) will be provided by the Office upon request and payment of the necessary fee.

FIG. 1 is a flow chart of a method of producing a biodegradable nanocomplex according to one embodiment of the present invention.

FIG. 2 shows the analysis results of the mean size of the biodegradable nanocomplex under different concentrations (1×-10×) of the mixture solution containing chitosan and polyglutamic acid in another embodiment of the present invention.

Figure 5A:
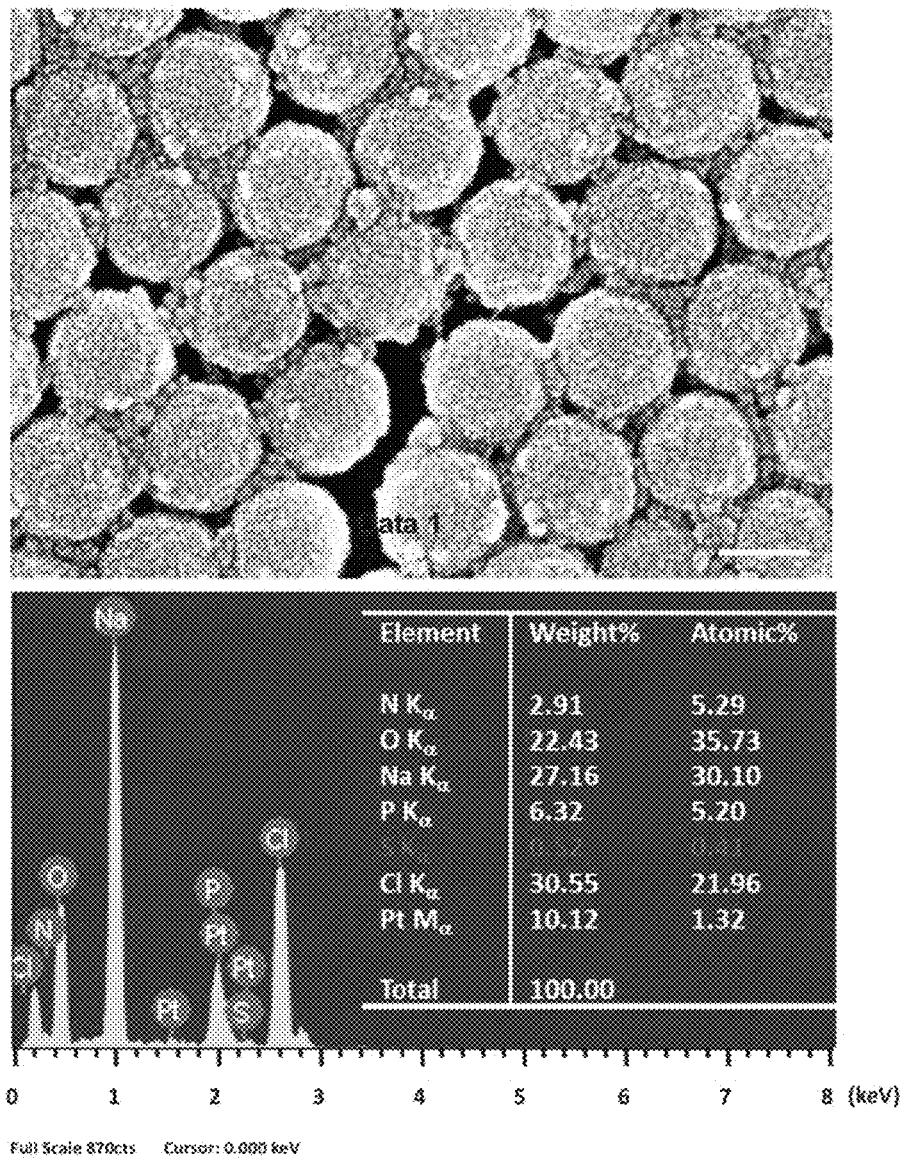
Figure 5B:
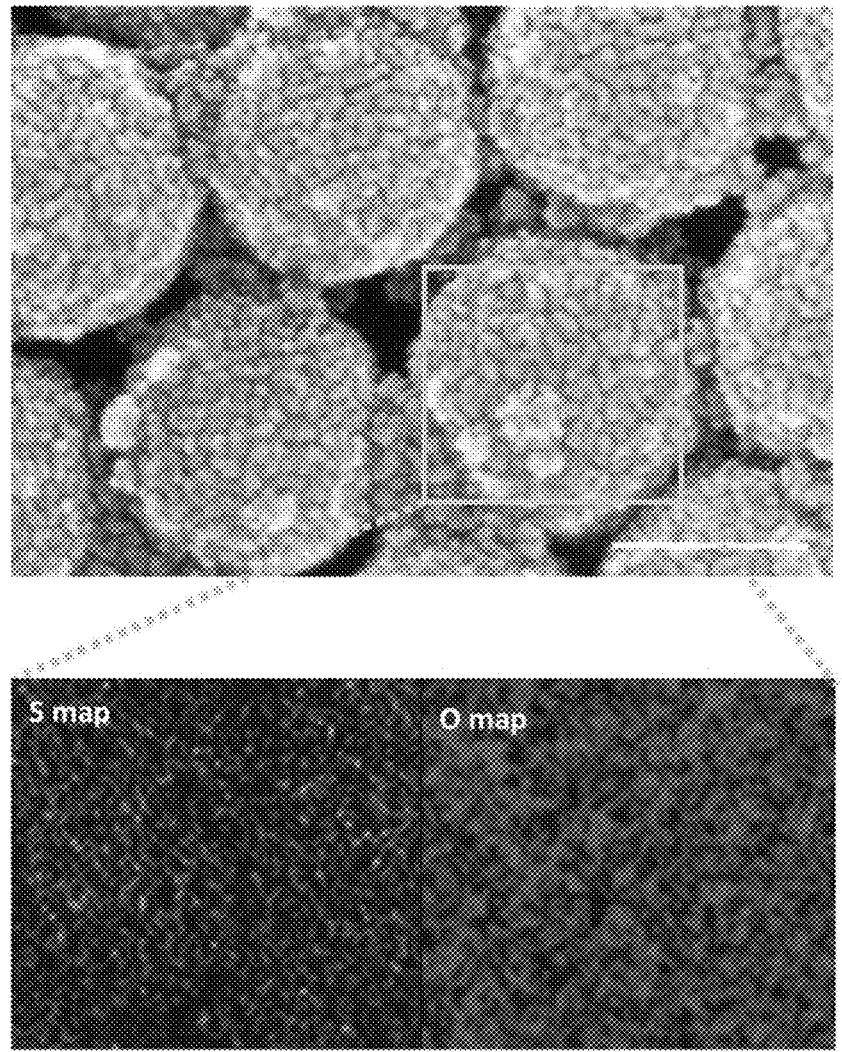
Figure 5C:
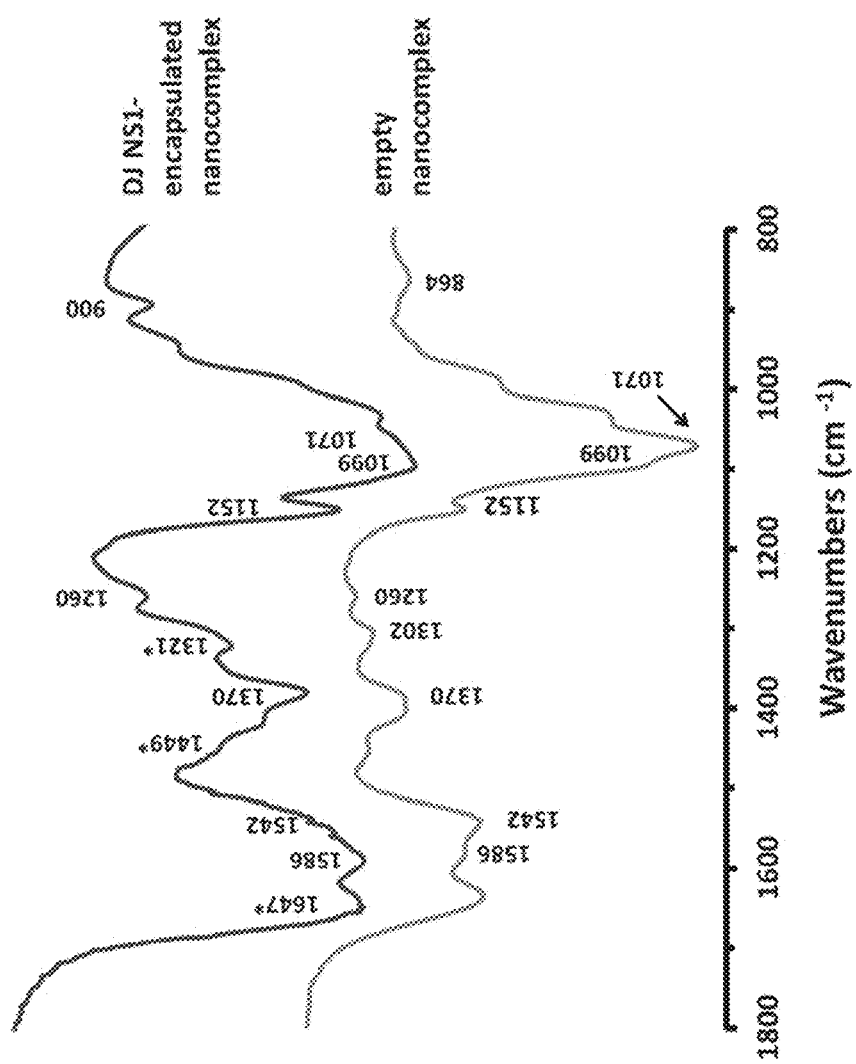
Figure 5D:
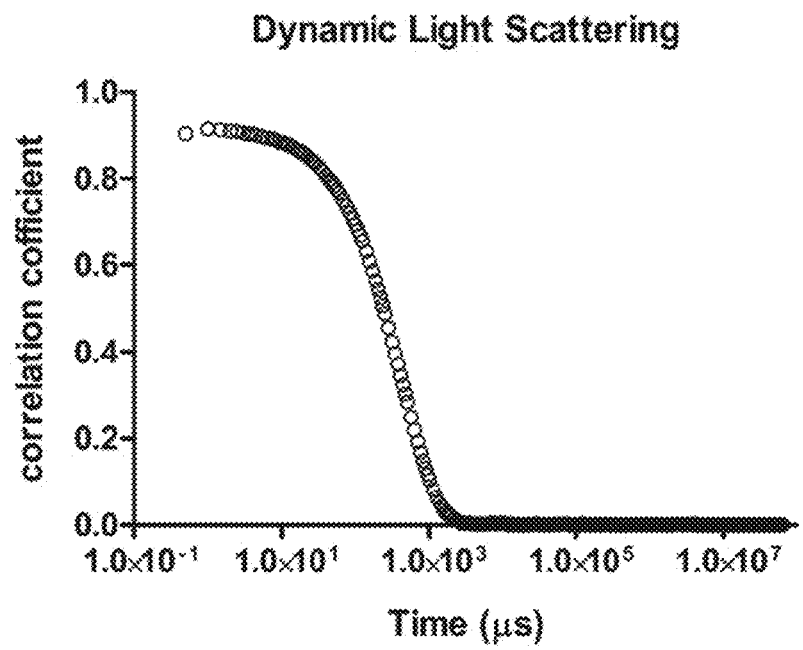
Figure 5E:
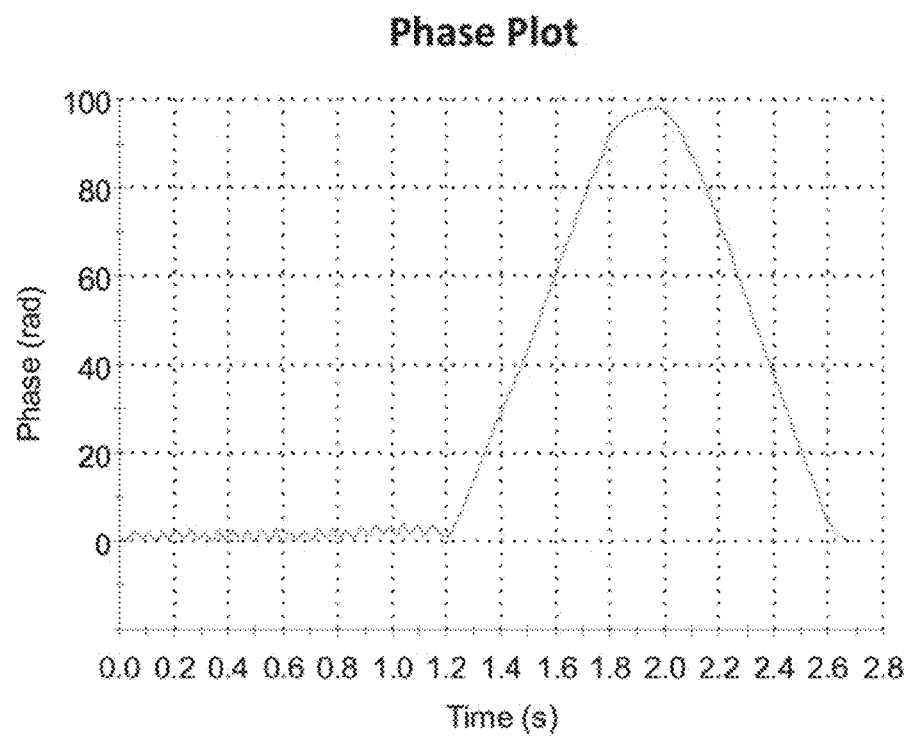

FIGS. 5a to 5e show morphological images and composition analysis profiles of DJ NS1-encapsulated nanocomplexes according to an embodiment of the present invention. FIG. 5a is a FESEM image at 50,000-folded (×) magnification, in which the lower panel is depicted to an energy-dispersive x-ray spectroscopy (EDX) spectra of DJ NS1-encapsulated nanocomplexes, and the sulfur (S, k-electron line) signal represents the cysteines of the DJ NS1 protein. FIG. 5b is a FESEM image at 150,000× magnification, the lower panel is depicted to FESEM image of DJ NS1-encapsulated nanocomplexes with corresponding elemental mapping images of oxygen and sulfur in the selected area, indicating the homogeneous distribution of DJ NS1 protein in nanocomplexes. FIG. 5c is an analysis profile of the nanocomplex composition by FTIR, in which the peaks labeled with an asterisk represent the characteristic vibration modes from specific protein structures. FIG. 5d is a profile of the stability of the biodegradable nanocomplexes measured by quasi-elastic light scattering (QELS) spectrometer (632 nm He—Ne laser, 10,000:1 polarity, 5 mW). FIG. 5e is an electrophoretic phase plot of the biodegradable nanocomplexes monitored by photon correlation spectrometer (PCL).

Figure 6A:
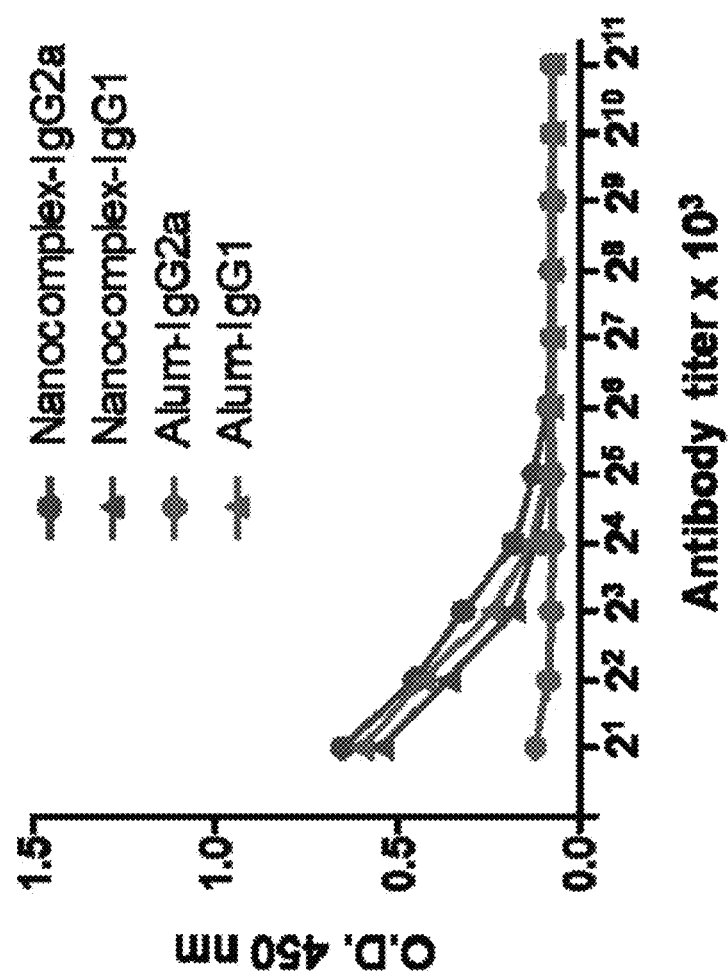
Figure 6B:
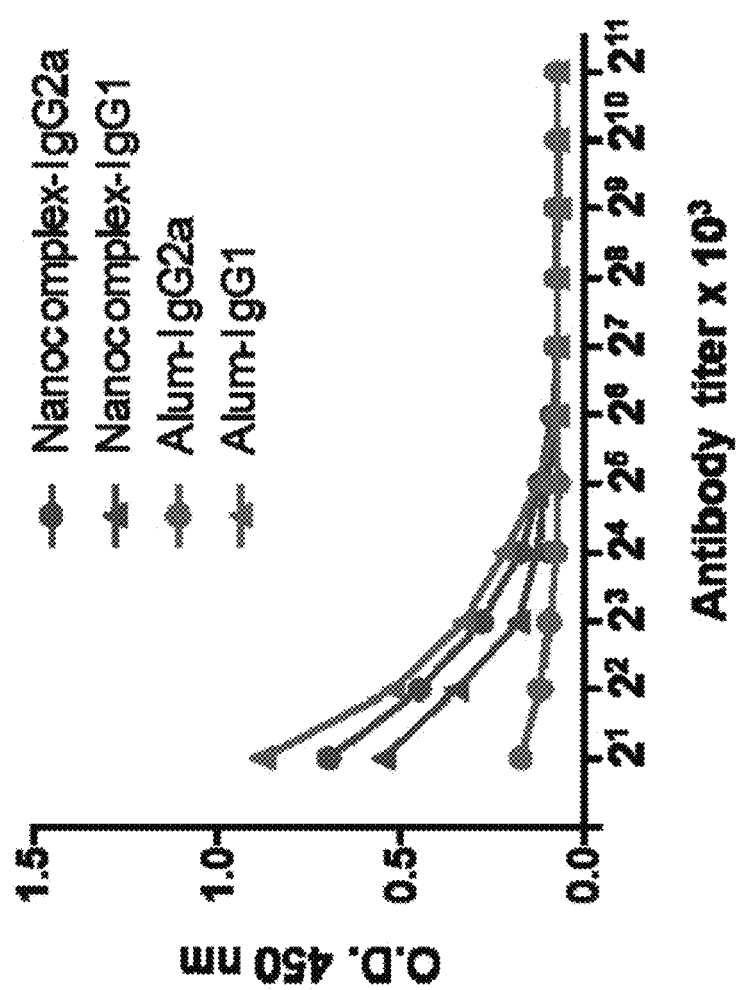
Figure 6C:
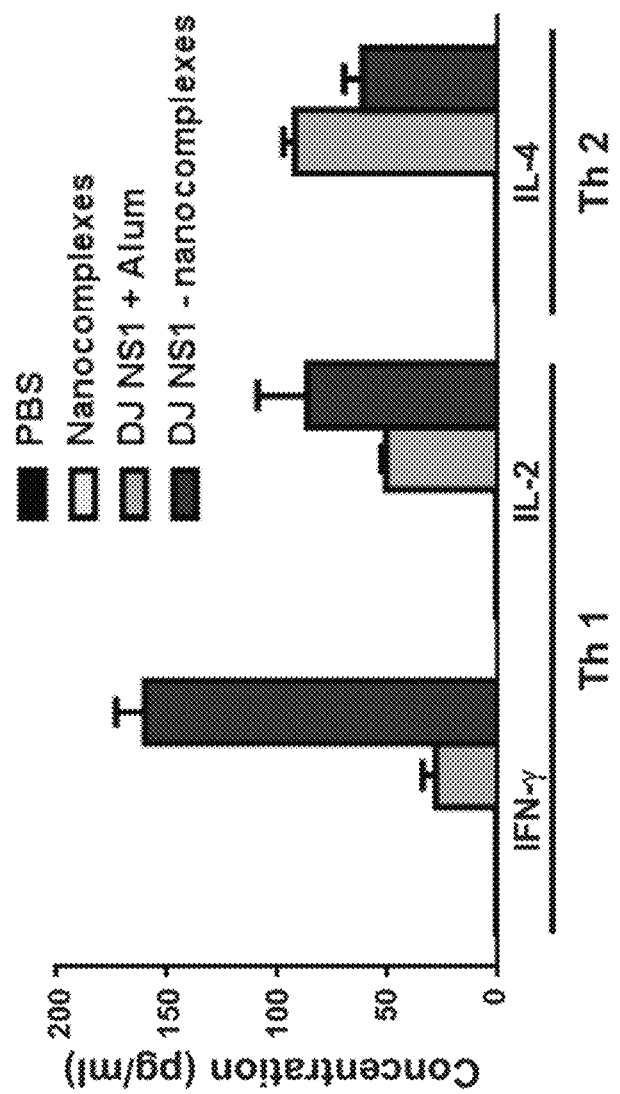

FIGS. 6a to 6c show antibody titers (FIGS. 6a and 6b) and cytokine profiles (FIG. 6c) of mice immunized with DJ NS1-encapsulated nanocomplexes or nanocomplexes alone according to an embodiment of the present invention.

Figure 7A:
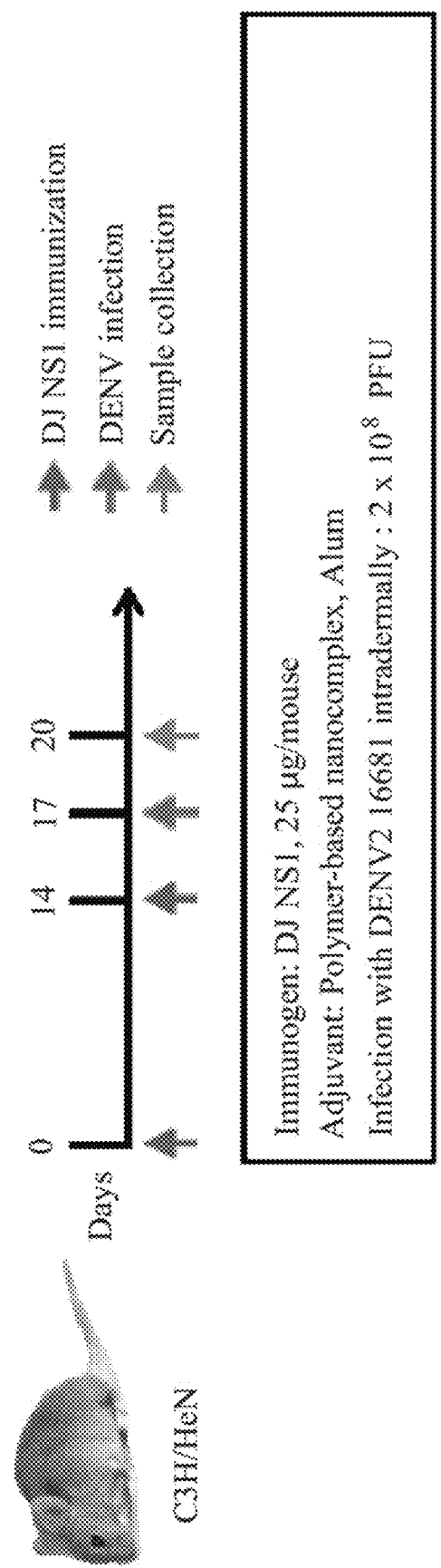
Figure 7B:
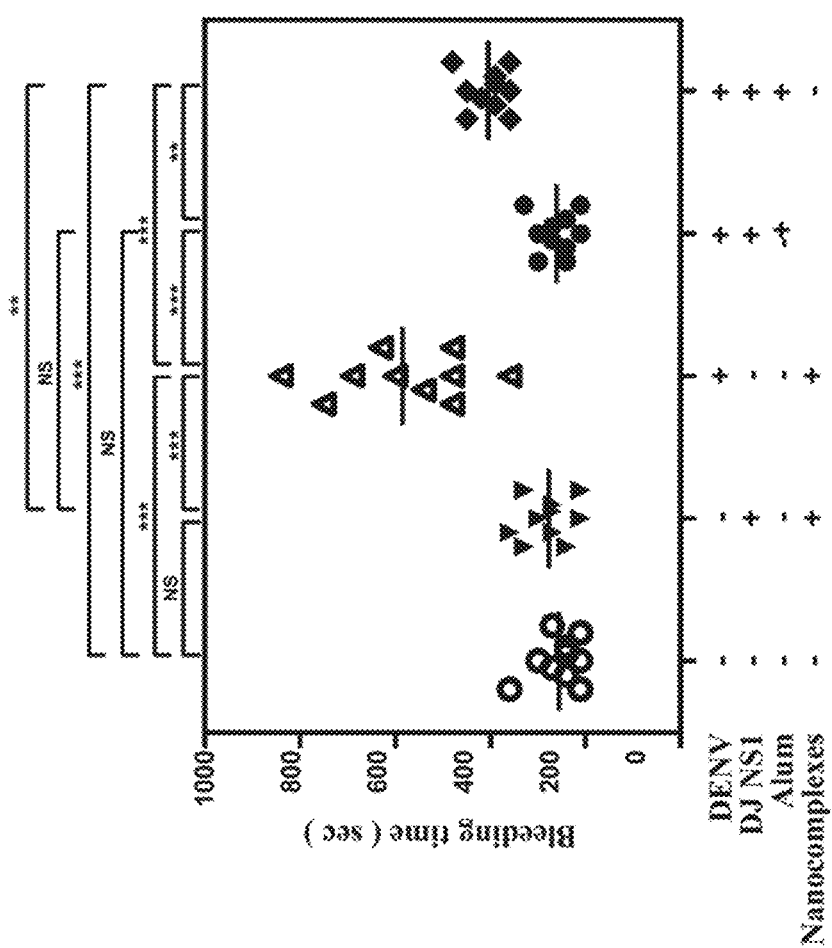

FIGS. 7a to 7b show active immunization results with DJ NS1-encapsulated nanocomplexes decreases DENV-induced prolonged bleeding time according to an embodiment of the present invention. FIG. 7a is an experimental design of the DENV-induced mouse hemorrhagic model in C3H/HeN mice. FIG. 7b is a dot diagram of Groups of mice (n=10) subcutaneously immunized twice with 25 μg/mouse of DJ NS1 protein in nanocomplexes or alum. The bleeding time was determined at 3 days post-infection. $P<0.01$, *$P<0.001$, NS: not significant; one-way ANOVA with Tukey's post-test.

Figure 8:
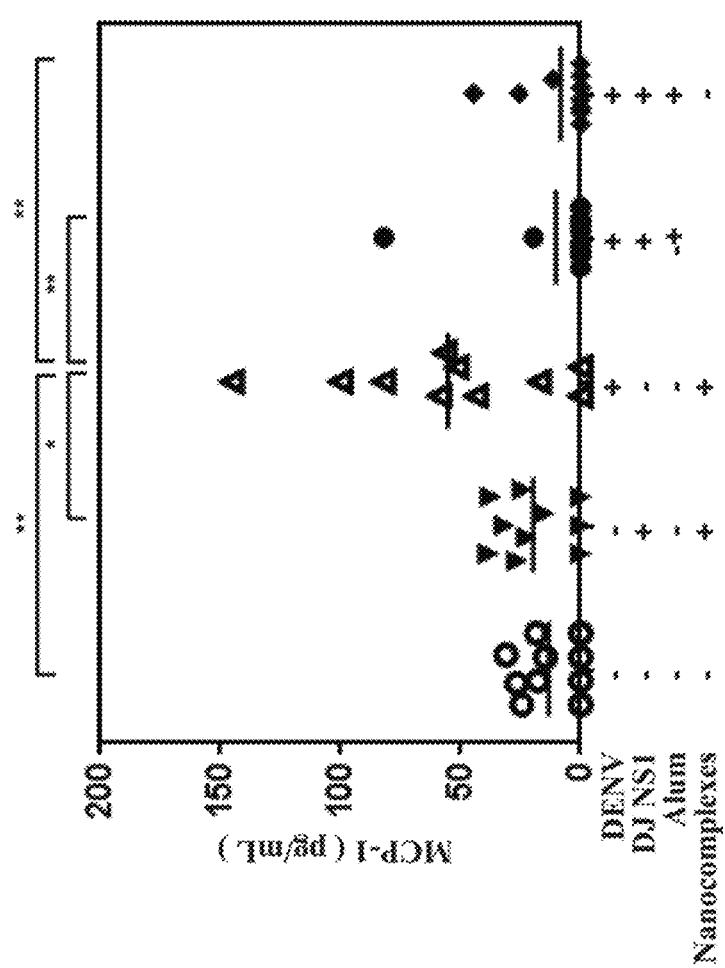

FIG. 8 shows an active immunization result with DJ NS1-encapsulated nanocomplexes reduces macrophage infiltration at the skin inoculation site according to an embodiment of the present invention. The mice were intradermally inoculated with medium (Mock) or DENV2 16681 ($2\times10^8$ PFU/mouse). The samples were collected at 3 days post-infection. FIG. 8 is a dot diagram of the concentrations of MCP-1 in mouse sera measured by Cytometric Bead Array.

Figure 9A:
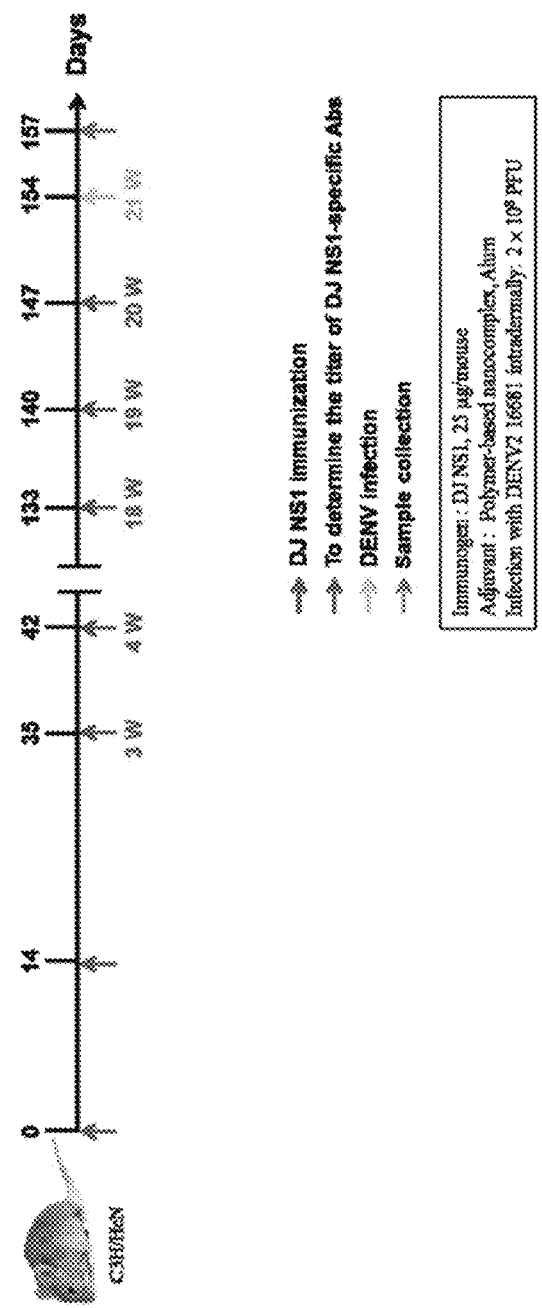
Figure 9B:
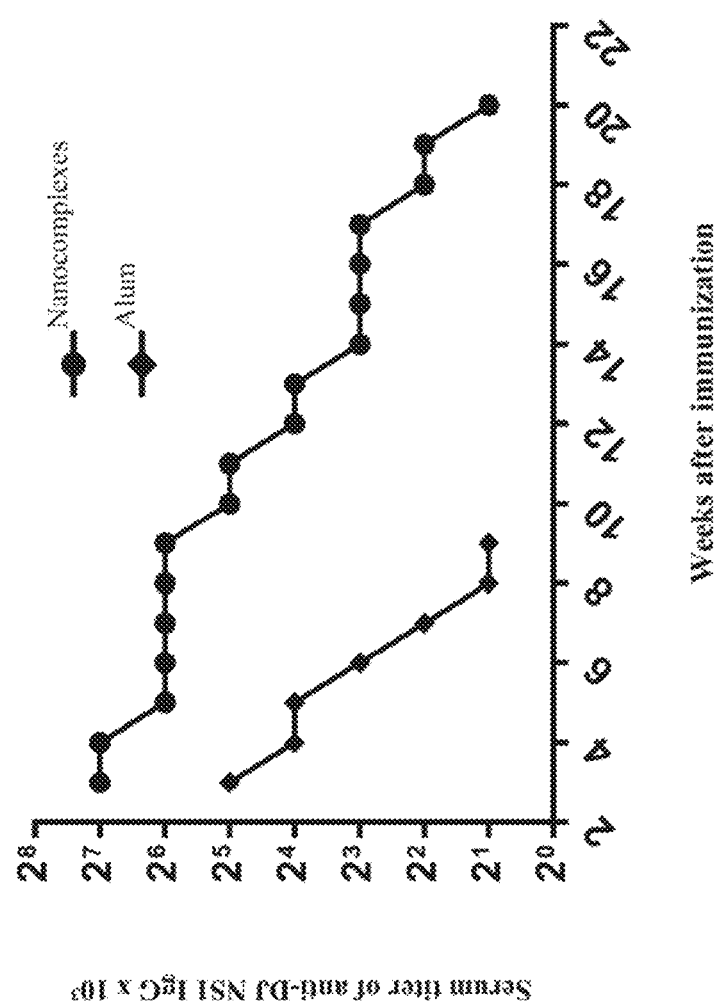
Figure 9C:
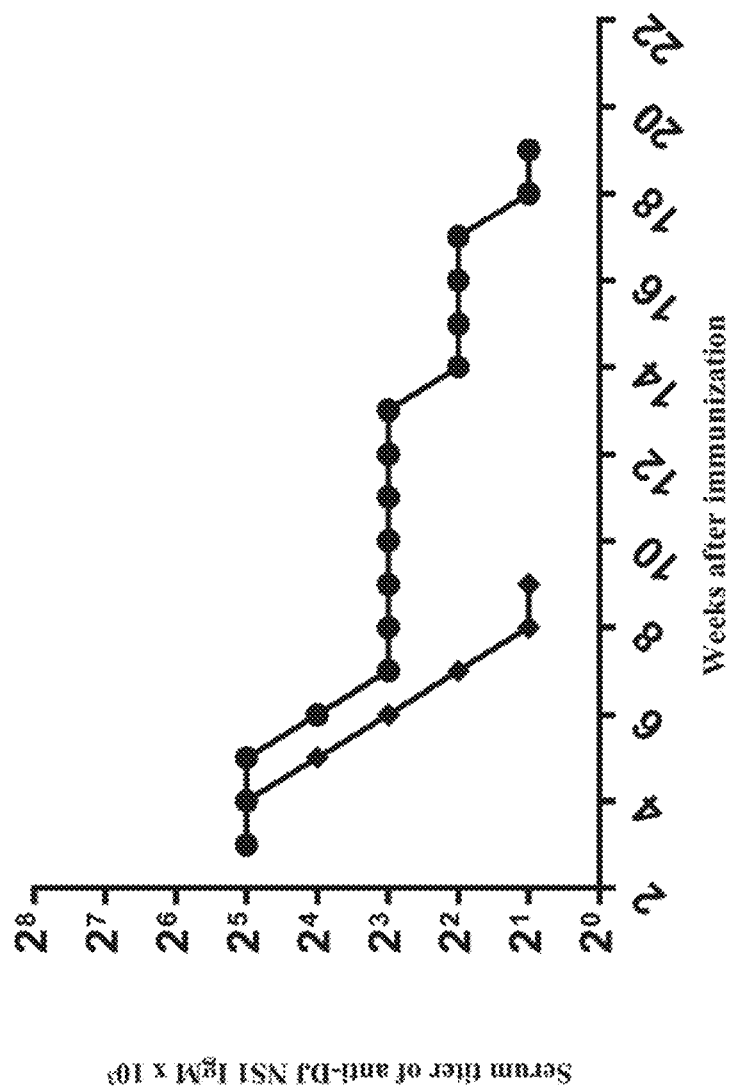
Figure 9D:
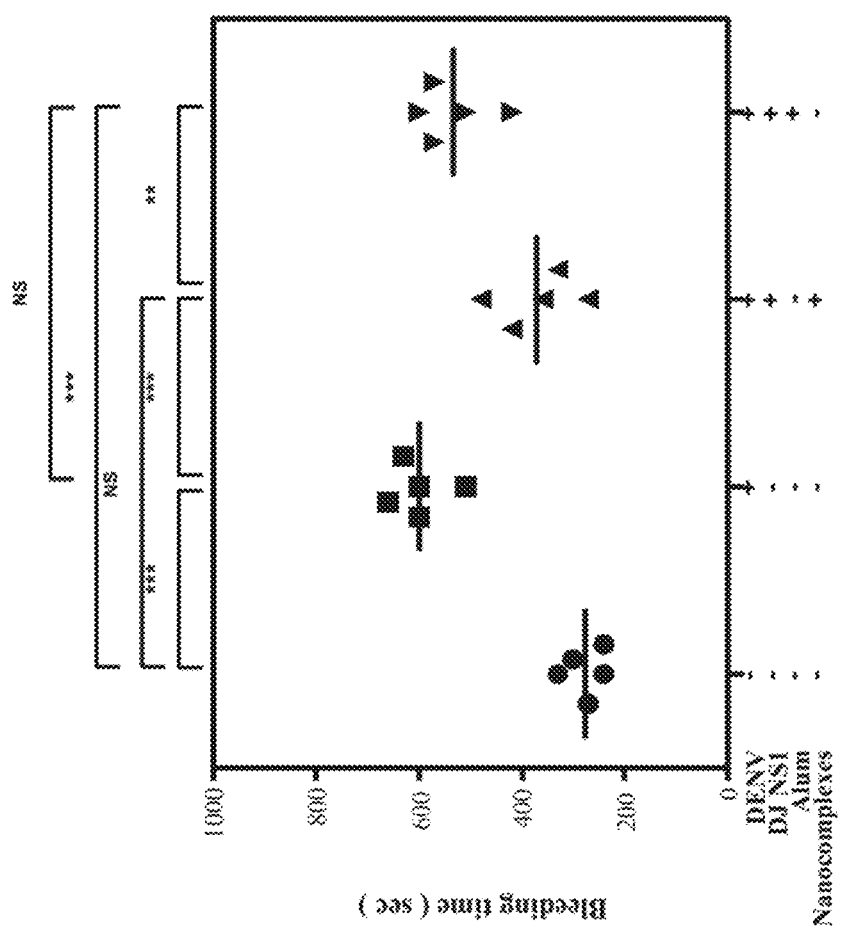

FIGS. 9a to 9d show DJ NS1 encapsulated nanocomplexes induce higher and longer-lasting DJ NS1-specific Ab responses than DJ NS1 with alum, and provide long-term protection. FIG. 9a is an experimental design of C3H/HeN mice subcutaneously immunized twice with 25 μg/mouse of DJ NS1 protein in nanocomplexes or alum. The DJ NS1-specific IgG (FIG. 9b) and IgM (FIG. 9c) titers in the sera from mice immunized with DJ NS1-encapsulated nanocomplexes or DJ NS1 plus alum were determined by ELISA. The dose of alum was 100 μg/mouse. FIG. 9d is a dot diagram of mice subsequently intradermally injected with medium (Mock) or DENV2 16681 ($2\times10^8$ PFU/mouse) at four sites on the upper back at 21 weeks after immunization. The bleeding time was determined at 3 days post-infection. (n=5/group) *$P<0.05$, ***$P<0.001$, NS: not significant; one-way ANOVA with Tukey's post-test.

Figure 10A:
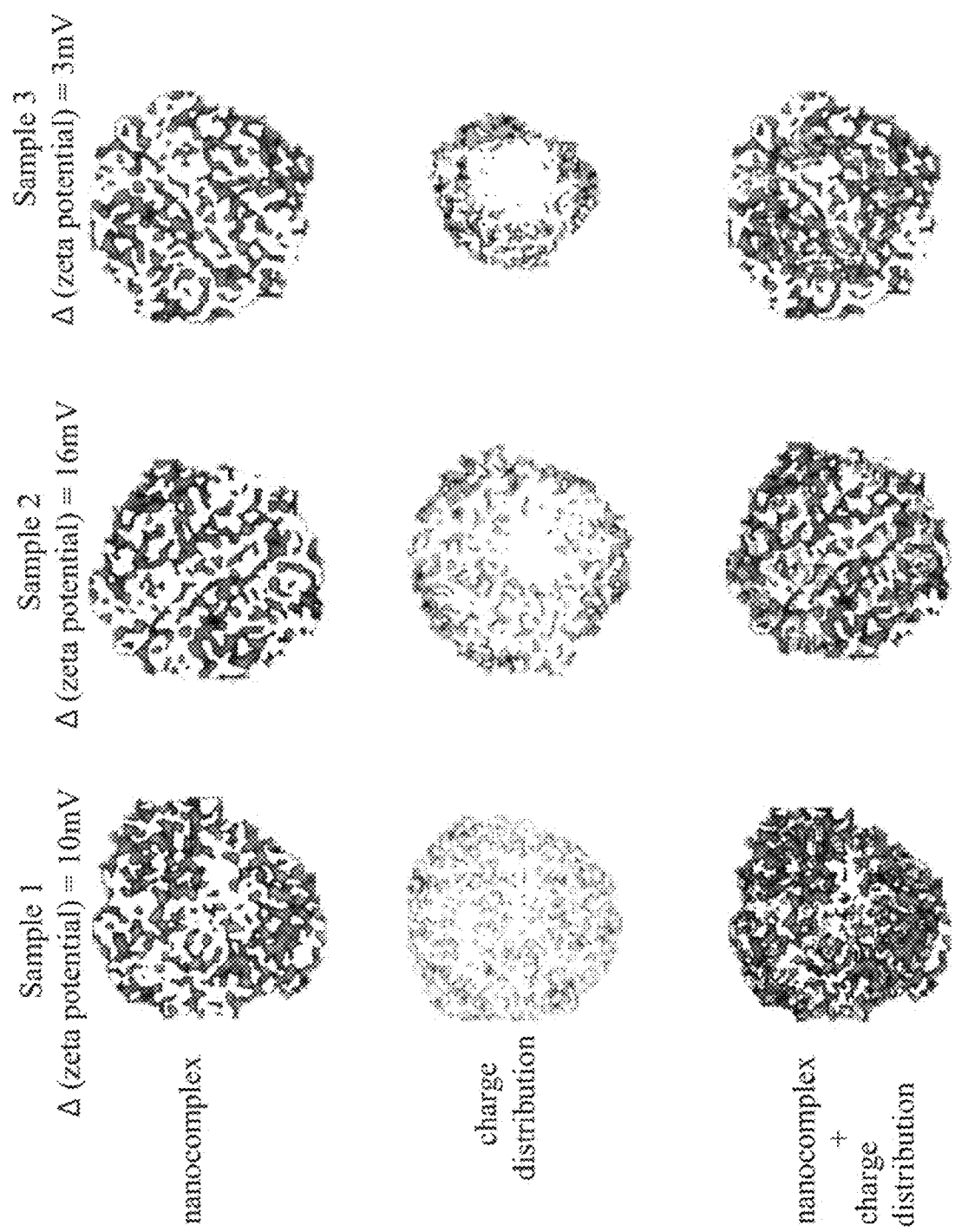
Figure 10B:
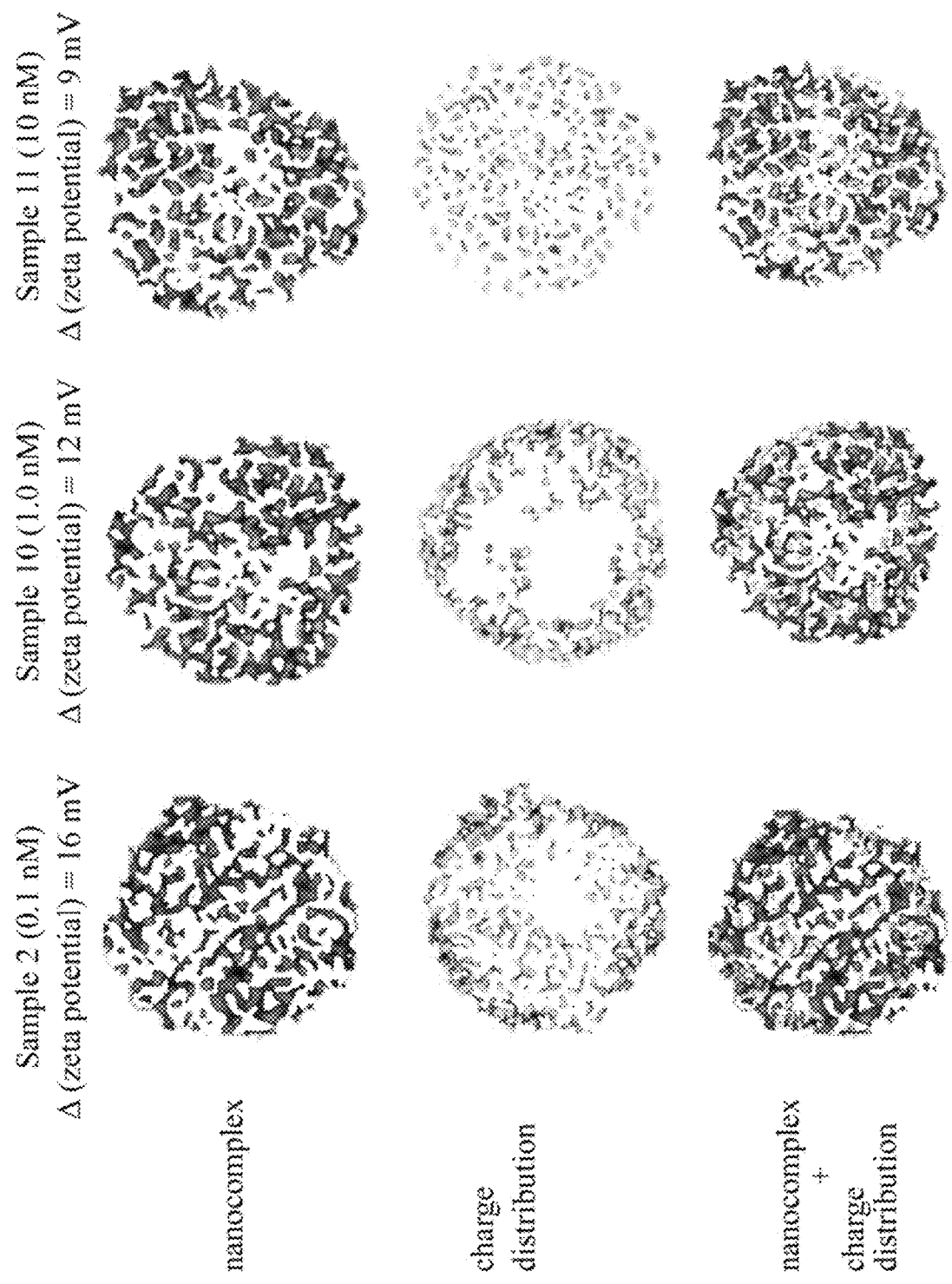

FIGS. 10a and 10b show images of molecular distributions (the images at the top row), the positively charge distributions (the images at the middle row) and the combined distributions (the images of nanocomplexes and charge distributions at the bottom row) of the nanocomplexes of Samples 1 to 3 (FIG. 10a) and Samples 2, 10 and 11 (FIG. 10b) of Example 8 according to some embodiments of the present invention.

Figure 11:
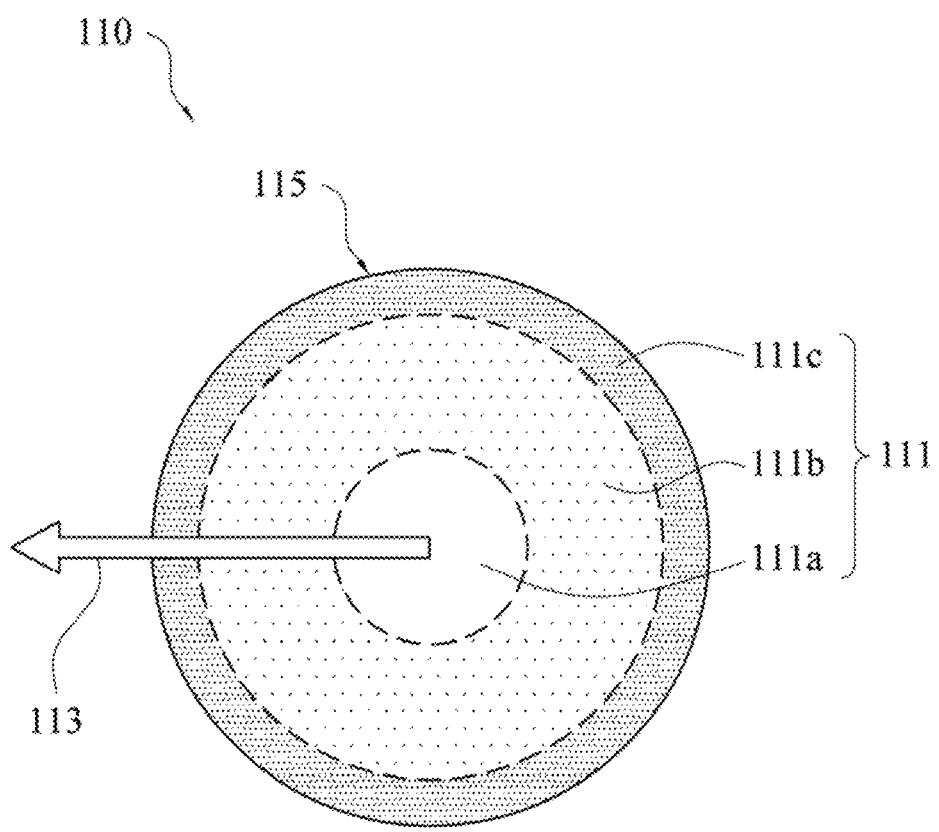
Figure 12A:
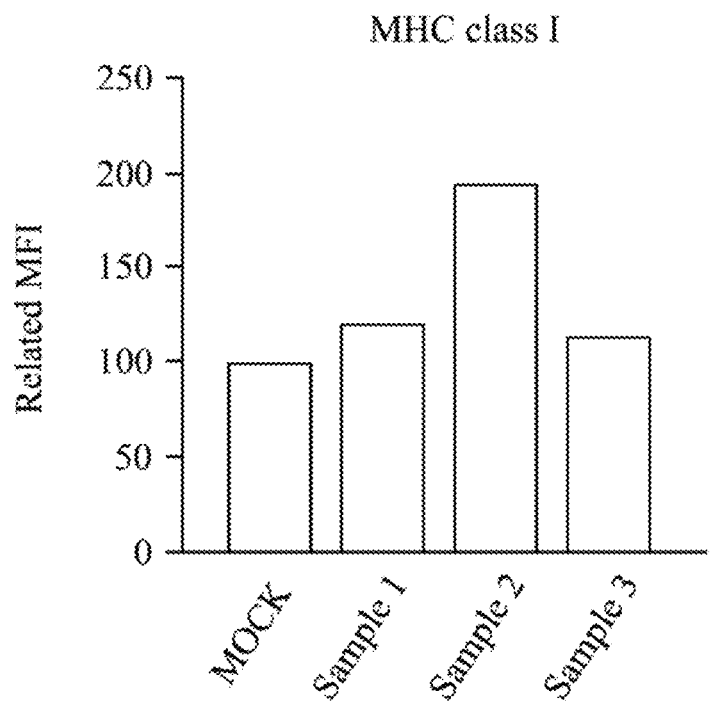
Figure 12B:
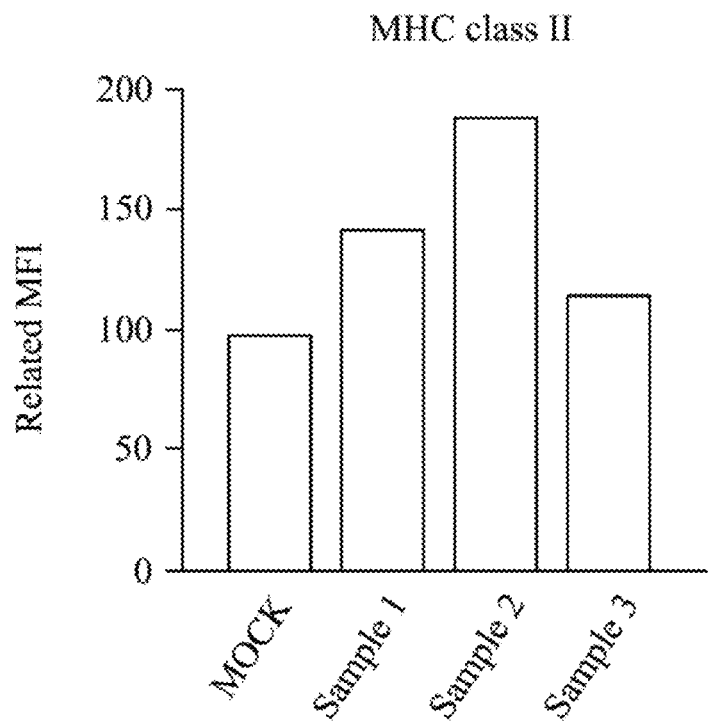
Figure 12C:
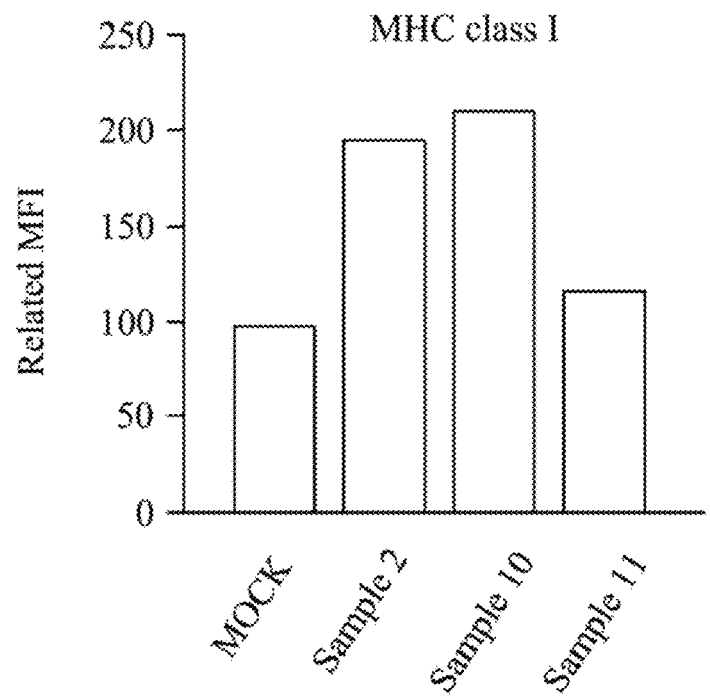
Figure 12D:
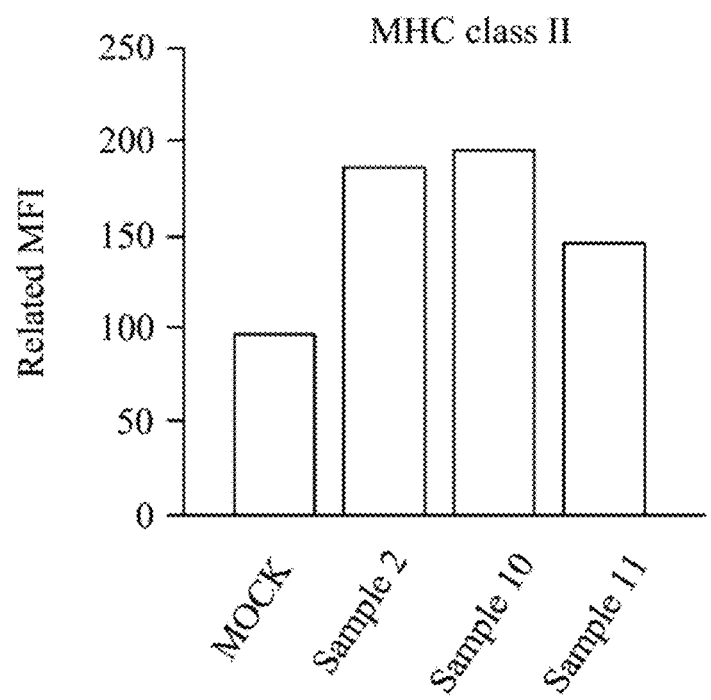

FIG. 11 shows a cross-sectional diagram of the nanocomplex of Sample 2 according to an embodiment of the present invention.

FIGS. 12a to 12d shows relative levels of antibodies to MHC class I (FIGS. 12a and 12c) and MHC class II (FIGS. 12b and 12d) of mice administrated with the nanocomplexes of Samples 1 to 3 (FIGS. 12a and 12b) and Samples 2, 10 and 11 (FIGS. 12c and 12d) of Example 8 according to embodiments of the present invention.

DETAILED DESCRIPTION

Hereinafter, various applications of the biodegradable nanocomplex will be described in more details referring to several exemplary embodiments below, while not intended to be limiting. Thus, one skilled in the art can easily ascertain the essential advantages and effects of the present invention and, without departing from the spirit and scope thereof, can make various changes and modifications of the invention to adapt it to various usages and conditions.

The present invention provides a biodegradable nanocomplex, which comprises a first electrically charged substance, a charge-redistribution substance, a second electrically charged substance and a carried substance, having a nonuniformally and positively charge distribution along a radial direction of the biodegradable nanocomplex, for holding the carried substance inside. In some embodiments, the nonuniformally and positively charge distribution of the present invention refers to such charge distribution comprising a first electrically charged portion having a first volume charge density, a second electrically charged portion surrounding the first electrically charged portion, and a third electrically charged portion surrounding the second electrically charged portion. The first volume charge density is substantially neutral. The third electrically charged portion comprises an outermost surface of the biodegradable nanocomplex. The biodegradable nanocomplex can modulate the carried substance towards the desired immune responses via the nonuniformally and positively charge distribution.

In an embodiment, the carried substance and first electrically charged substance are negatively charged. The aforementioned carried substance can be negatively charged or positively charged, for example, being selected from the group consisting of nucleic acids, peptides, biological drugs (for examples, recombinant proteins, antibodies), small molecular compounds, viruses, bacteria, and cells. The nucleic acid can include deoxyribonucleic acid (DNA), ribonucleic acid (RNA), or peptide nucleic acids (PNA). In some examples, the carried substance can include a recombinant viral protein DJ NS1 (negatively charged) or cytochrome c (positively charged).

In some embodiments, the nonuniformally and positively charge distribution comprises a first electrically charged portion having substantially electrical neutrality, a second electrically charged portion surrounding the first electrically charged portion, and a third electrically charged portion surrounding the second electrically charged portion. In an example, the third electrically charged portion comprises an outermost surface of the biodegradable nanocomplex.

In an example, the carried substance and first electrically charged substance are negatively charged. In this example, the second electrically charged substance is positively charged, and the charge-redistribution substance can be negatively charged or positively charged.

Alternatively, in another example, the carried substance and first electrically charged substance are positively charged, the second electrically charged substance can be positively charged, and the charge-redistribution substance can be negatively charged or positively charged.

In the aforementioned examples, the first electrically charged substance, the charge-redistribution substance and/or the second electrically charged substance are respectively selected from the group consisting of chitosan (CS), gelatin, cationic cyclodextrin, cationic dextran, poly(L-lysine), polyethylenimine (PEI) and polyamidoamine when the first electrically charged substance, the charge-redistribution substance and/or the second electrically charged substance are positively charged.

In the aforementioned examples, the first electrically charged substance and/or the charge-redistribution substance are respectively selected from the group consisting of γ-polyglutamic acid (γ-PGA) and heparin when the first electrically charged substance and/or the charge-redistribution substance are negatively charged.

In some embodiments, the biodegradable nanocomplex has a zeta potential of +10 mV to +40 mV.

For the purpose of maintaining the nonuniformally and positively charge distribution, a molar ratio of the charge-redistribution substance to the first electrically charged substance is 0.05 to 1.00, preferably 0.06 to 0.70, and more preferably 0.0625 to 0.625.

Figure 1:
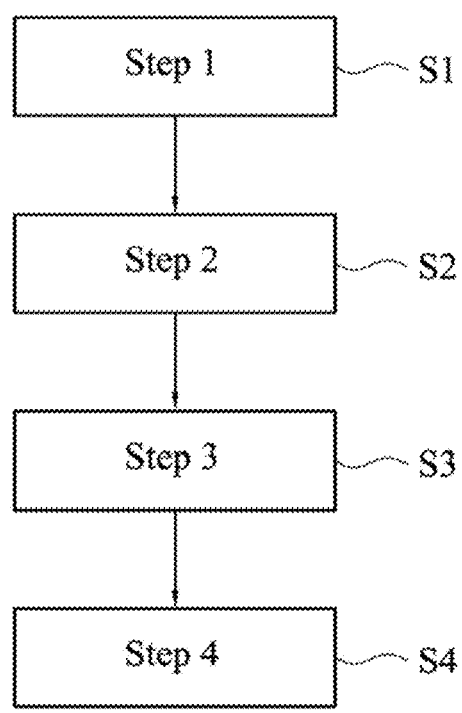

The biodegradable nanocomplex can be produced by a method as follows. FIG. 1 is a flow chart of a method for making the aforementioned biodegradable nanocomplex according to one embodiment of the present invention. In an embodiment of the method, zeta potentials of the first electrically charged substance, the charge-redistribution substance, the second electrically charged substance and the carried substance can be measured respectively, as shown in the Step 1 (S1) of FIG. 1.

And then, the carried substance can be added into a first solution of the first electrically charged substance, thereby forming a dispersion, in which the first electrically charged substance and the carried substance have the same polarity, as shown in the Step 2 (S2) of FIG. 1.

Next, a zeta potential of the dispersion can be adjusted by adding the charge-redistribution substance into the dispersion, in which a molar ratio of the charge-redistribution substance to the first electrically charged substance is 0.05 to 1.00, preferably 0.06 to 0.70, and more preferably 0.0625 to 0.625, as shown in the Step 3 (S3) of FIG. 1.

Subsequently, the second electrically charged substance can be added into the dispersion, thereby forming the biodegradable nanocomplex for holding the carried substance inside, as shown in the Step 4 (S4) of FIG. 1, thereby modulating the carried substance towards the desired immune responses via the nonuniformally and positively charge distribution.

Optionally, after the Step 4 (S4) of FIG. 1, according to a desired particle size of the biodegradable nanocomplex, the mole number of the first electrically charged substance and the second electrically charged substance in the dispersion can be proportionally adjusted. The particle size of the carrier is positively correlated with the mole number of a solute in the dispersion, for obtaining the biodegradable nanocomplex with a desired particle size.

Alternatively, the biodegradable nanocomplex in the dispersion can be filtrated and formed to the biodegradable nanocomplex. The particle size of the biodegradable nanocomplex is between micrometers to nanometers. In an embodiment of the present invention, the biodegradable nanocomplex has an average particle size of 40 nm to 10 μm and a zeta potential of 10 mV to 40 mV.

Thereinafter, various applications of the biodegradable nanocomplex and the method for making the same will be described in more details referring to several exemplary embodiments below, while not intended to be limiting. Thus, one skilled in the art can easily ascertain the essential characteristics of the present invention and, without departing from the spirit and scope thereof, can make various changes and modifications of the invention to adapt it to various usages and conditions.

EXAMPLES OF PREPARATION

1. Prepare a First Solution Comprising a First Electrically Charged Substance

In detail, the first electrically charged substance was exemplified as polyglutamic acid. A proper amount of polyglutamic acid is added into de-ionized water and stirred by electromagnetic stirrer until the polyglutamic acid is totally dissolved. Then, the polyglutamic acid solution is removed the sodium by membrane dialysis. The dialysis process is accomplished at 4° C. for preventing bacterial growth. After dialysis, the polyglutamic acid solution is put at −20° C. for being totally frozen. Then, the water content of the frozen polyglutamic acid solution is removed by lyophilization to obtain the crystallized powder of the polyglutamic acid. The crystallized powder of the polyglutamic acid is stored in a sterilized tube and put in a moisture-proof box. Finally, a proper amount of crystallized powder of the polyglutamic acid is taken and dissolved in the de-ionized water in a desired concentration, which is the first solution comprising the first electrically charged substance with negative charge.

2. Prepare a Second Solution Comprising a Second Electrically Charged Substance

According to a desired zeta potential of a biodegradable nanocomplex, a second solution containing a second electrically charged substance is prepared and added into the first solution. In detail, the second electrically charged substance is chitosan. 5 g low-viscous chitosan is added into 495 ml de-ionized water with 5 ml glacial acetic acid and stirred by electromagnetic stirrer until the chitosan solution stays in a yellow and pellucid state. It is worth noted that $NH_2$ of the chitosan is converted to $NH_3^+$ under an acidic condition, so the chitosan is positively charged. Moreover, the acetylation degree of the chitosan influences the ratio of the positive electric charge on the chitosan. For example, when the acetylation degree of the chitosan is 100%, the $NH_2$ of the chitosan is totally converted to $NH_3^+$; however, if the acetylation degree of the chitosan is less than 100%, there are acetyl groups on the chitosan, and those acetyl groups are not positively charged under an acidic condition, so the total quantity of positive charge of the chitosan is decreased.

Accordingly, more chitosan must be added into the de-ionized water with glacial acetic acid to reach the desired quantity of positive charge in the chitosan solution.

Next, the glacial acetic acid in the chitosan solution is removed by membrane dialysis. The pH of the chitosan solution is about 6.5 after dialysis. Then, the chitosan solution is filtrated by air suction filter to remove the impurity. Finally, the chitosan solution is heated and stirred at 135° C. for being concentrated until the concentration of the chitosan solution reaches 20-30 mg/ml, which is the second solution comprising the second electrically charged substance with positive charge.

It was noted that the aforementioned first and second electrically charged substance can be naturally biodegradable macromolecules, such as heparin or polyglutamic acid, and chitosan or collagen, respectively. The aforementioned first and second electrically charged substance also can be synthetic biodegradable macromolecules.

3. Preparation of Recombinant Chimeric DJ NS1 Proteins

This procedure was followed as previously reported by Wan, S. W. et al. in *PLoS One* 9, e92495 (2014), the entirety of which was incorporated by reference herein. Briefly, DJ NS1 (a.a. 1-270 of DENV NS1 and a.a. 271-352 of JEV NS1) cDNA was cloned into the pET28a vector with histag. The plasmids were prepared by the Proteomic Research Core Facility, Academia Sinica. Following introduction of the plasmids into *Escherichia coli* BL21, the recombinant proteins were induced by 1 M isopropyl B-D-1-thiogalactopyranoside (IPTG) (Calbiochem), solubilized in urea buffer (8 M urea, 500 mM NaCl, and 20 mM Tris-HCl) and purified on a $Ni^{2+}$ column (GE Healthcare Life Science). After purification, proteins were examined using 10% sodium dodecyl sulfate polyacrylamide gel electrophoresis (SDS-PAGE), followed by staining with Coomassie brilliant blue R250. Purified proteins were dialyzed in refolding buffer (50 mM Tris-HCl, 50 mM NaCl, 2 mM reduced glutathione, 0.2 mM oxidized glutathione, 1 mM EDTA, and 0.1 mM PMSF) and concentrated by Amicon Ultra (Millipore).

4. Form and Filtrate a Mixture Solution to Obtain a Biodegradable Nanocomplex 5 ml polyglutamic acid solution of Example 1 was mixed with 6 ml chitosan solution of Example 2 to form a 11 ml mixture solution, and the mixture solution is stirred for 2 minutes. In the mixture solution, the total dry weight of the polyglutamic acid and the chitosan is 2 mg. The concentration of the aforementioned mixture solution is as one-fold (1×) concentration to be the standard concentration of the mixture solution in the following experiment. The 11 ml mixture solution is filtrated to obtain the biodegradable nanocomplex. The zeta potential of the biodegradable nanocomplex is 13 mV, and the particle size of the same is 40 nm.

Table 1 shows the charge ratio and the weight ratio of chitosan (CS) to polyglutamic acid (γ-PGA), and the particle size and the zeta potential of the aforementioned biodegradable nanocomplex. The N/A means that the data is undetectable by dynamic light scattering (DLS) because of the precipitation of the biodegradable nanocomplex. The type of DLS is Zetasizer Nano Serie (3000HS, Malvern Instruments, Worcestershire, UK).

TABLE 1

| Charge ratio CS:γ-PGA | Weight ratio CS:γ-PGA | Size (nm) | Zeta potential (mV) |
|---|---|---|---|
| 4:1 | 1.704:0.296 | 40.49 ± 0.8415 | 13.2 ± 0.354 |
| 3:1 | 1.624:0.376 | N/A | N/A |
| 2:1 | 1.484:0.516 | N/A | N/A |

5. Proportionally Adjust the Mole Number of Solute in the Mixture Solution

According to the desired particle size of the biodegradable carrier, the mole number of the first electrically charged substance and the second electrically charged substance is proportionally adjusted in the mixture solution. Based on the method for preparing 1× mixture solution, five-fold (5×) and ten-fold (10×) mixture solution are prepared. Table 2 shows the charge ratio and the weight ratio of chitosan (CS) to polyglutamic acid (γ-PGA), and the particle size and the zeta potential of the biodegradable carrier produced from 5× and 10× mixture solution.

TABLE 2

| Charge ratio CS:γ-PGA | | Weight ratio CS:γ-PGA | Size (nm) | Zeta potential (mV) |
|---|---|---|---|---|
| 5X | 4:1 | 8.52:1.48 | 64.77 ± 0.2546 | 12.5 ± 1.481 |
| | 3:1 | 8.12:1.88 | N/A | N/A |
| | 2:1 | 7.42:2.58 | N/A | N/A |
| 10X | 4:1 | 17.04:2.96 | 84.46 ± 1.662 | 12.8 ± 0.071 |
| | 3:1 | 16.26:3.76 | N/A | N/A |
| | 2:1 | 14.84:5.16 | N/A | N/A |

As shown in Table 1 and Table 2, whatever the biodegradable carrier is produced from mixture solution with one-fold, five-fold, or ten-fold concentration, the biodegradable carrier is stable under the charge ratio of CS to γ-PGA being 4:1. However, the precipitation was happened while the chitosan solution and the polyglumatic acid were mixed under the other charge ratios of CS to γ-PGA, such as 3:1 or 2:1.

Figure 2:
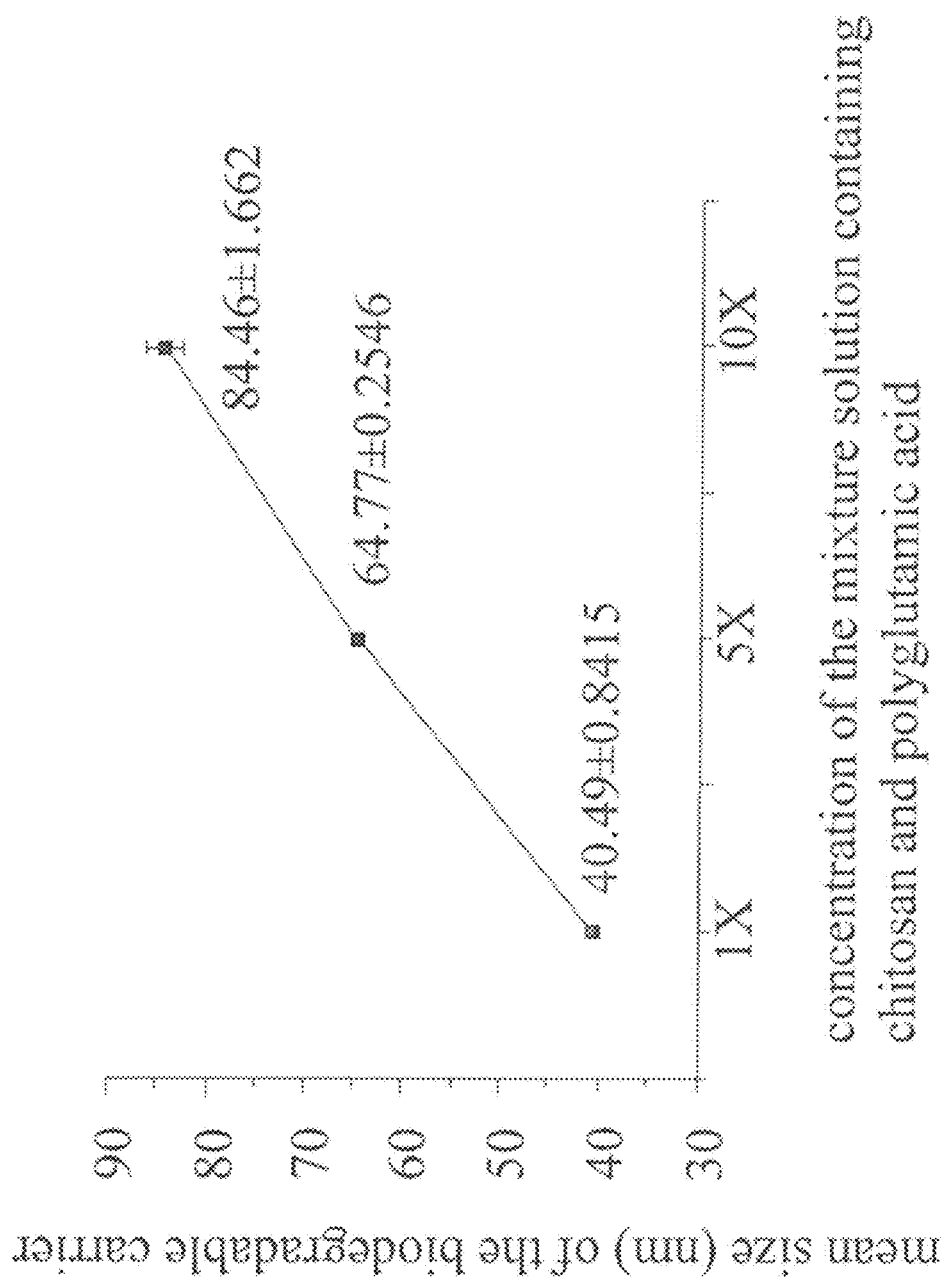

FIG. 2 further showed the analysis results of the mean size of the biodegradable carrier under different concentrations (1×-10×) of the mixture solution containing chitosan and polyglutamic acid in another embodiment of the present invention. As shown in FIG. 2, it was obvious to know that the mean size of the biodegradable carrier is bigger as the concentration of the mixture solution is higher. The concentration of mixture solution showed a linear relationship with the mean size of the biodegradable carrier. Therefore, the biodegradable carrier was obtained through setting the desired zeta potential of the biodegradable carrier first and then adjusting the concentration of the mixture solution for forming the biodegradable carrier with the desired particle size. Table 3 showed the weight ratio of chitosan (CS) to polyglutamic acid (γ-PGA), and the particle size and the zeta potential of the biodegradable carrier produced from mixture solution with 1×-35× concentration under the charge ratio of CS to γ-PGA was 4:1.

TABLE 3

| Mixture solution concentration | Weight ratio CS:γ-PGA | Size (nm) | Zeta potential (mV) |
|---|---|---|---|
| 1X | 1.704:0.296 | 40.49 ± 0.8415 | 13.2 ± 0.354 |
| 5X | 8.52:1.48 | 64.77 ± 0.2546 | 12.5 ± 1.481 |

TABLE 3-continued

| Mixture solution concentration | Weight ratio CS:γ-PGA | Size (nm) | Zeta potential (mV) |
|---|---|---|---|
| 10X | 17.04:2.96 | 84.46 ± 1.662 | 12.8 ± 0.071 |
| 20X | 34.08:5.92 | 267.0 ± 3.889 | 13.1 ± 0.071 |
| 25X | 42.6:7.4 | 335.2 ± 0.8485 | 13.4 ± 0.071 |
| 30X | 51.12:8.88 | 364.0 ± 4.313 | 12.6 ± 0.424 |
| 35X | 59.64:10.36 | 460.9 ± 5.657 | 12.9 ± 0.424 |

As shown in Table 3, as the mole number of solute in the mixture solution was higher, the mean size of the biodegradable carrier was bigger, but the zeta potential of the biodegradable carrier was similar. It was corresponding to the characteristics of the positive relationship between the particle size of the biodegradable nanocomplex and the mole number of solute in the mixture solution.

Figure 3:
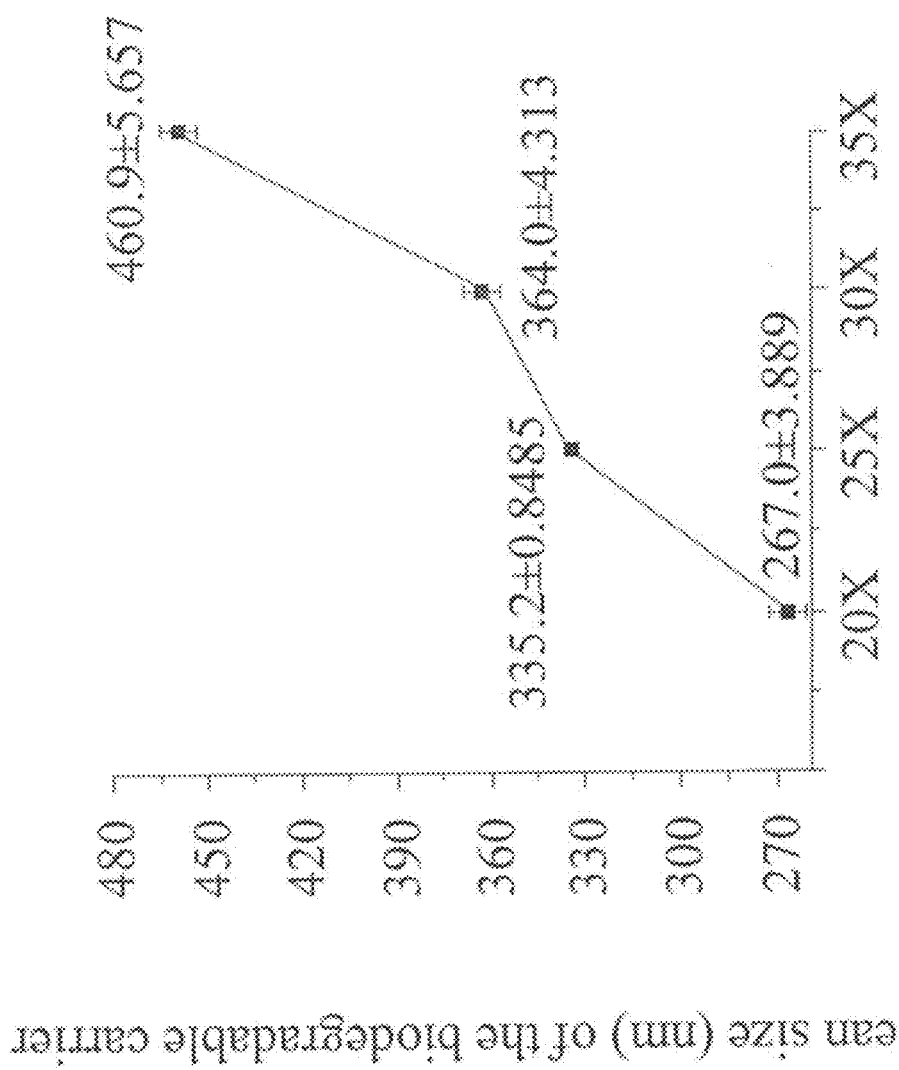
FIG. 3 shows the analysis results of the mean size of the biodegradable nanocomplex under different concentrations (20×-35×) of the mixture solution containing chitosan and polyglutamic acid in the other embodiment of the present invention.

FIG. 3 showed the analysis results of the mean size of the biodegradable nanocomplex under different concentrations (20×-35×) of the mixture solution containing chitosan and polyglutamic acid in the other embodiment of the present invention. The trend of the mean sizes of the biodegradable nanocomplex under different concentrations approximately corresponded to the prospect.

Accordingly, the mixing ratio of the first electrically charged substance to the second electrically charged substance in the method of producing the biodegradable nanocomplex with adjustable zeta potentials and particle sizes of the present invention could be adjusted according to different applications of the biodegradable nanocomplex. The desired zeta potential of the biodegradable nanocomplex was set first, and then the concentration of the mixture solution was adjusted for making the biodegradable nanocomplex with the desired particle size. In the other word, the zeta potential and the particle size of the biodegradable nanocomplex could be adjusted arbitrarily in order that there were different application strategies for meeting the need of the different carried substances with different physical and chemical properties. For example, in the application of targeted drug, the DNA vaccine development and the anti-cancer drug delivery, the carried substance was delivered to the target successfully because the physical and chemical properties of the biodegradable nanocomplexes are adjusted. The effect of the drug delivery was greatly increased, and the dose and the side effect of the carried substance were decreased. Moreover, because the particle size of the biodegradable nanocomplex was uniform and the biodegradable nanocomplex was charged, the problem of the aggregation and fusion of the traditional liposome could be overcome. In addition, the method of producing the biodegradable nanocomplex of the present invention was quite simple, excluding conventional solvent evaporation step and hydration step, so that the cost was greatly decreased. The biodegradable nanocomplex also had better dispersivity in the mixture solution and was not aggregated during the dry process. Therefore, the biodegradable nanocomplex could be kept as dry powder for resolving the problem that the previous liposome had to be kept in the suspension, thereby decreasing the shipping cost.

6. Preparation and Characterization of Biodegradable Nanocomplexes

A low-MW CS was obtained from the depolymerization of a commercially available CS. The low-MW and polycationic CS had a good solubility at a pH value close to physiological range. CS (MW 280 kDa) with a degree of deacetylation of approximately 85% (Sigma-Aldrich, St. Louis, Mo., USA) was treated with sodium perborate tetrahydrate ($NaBO_3$, Sigma-Aldrich) to produce low-MW CS. A sample of 25 μg of DJ-NS1 protein (negatively charged, −) or cytochrome c (positively charged, +) was premixed with aqueous γ-PGA (1 mg/ml, 5 ml) and added into aqueous CS (6 mg/ml, 0.5 ml) under magnetic stirring in the 10 mM phosphate buffer (pH=6) at room temperature (approximately 4° C. to 40° C.). The samples were concentrated to ¹⁄₁₀ of volume and stored at 4° C.

The particle size and zeta potential of the prepared nanoparticles were measured using a quasi-elastic light scattering (QELS) analyzer (3000HS, Malvern Instruments, Worcestershire, UK). FT-IR was recorded on a NEXUS 670 spectrometer equipped with a liquid nitrogen-cooled MCT detector by using the attenuated total reflectance (ATR) technique. The spectra were obtained by 1000 scans with a resolution of 1 $cm^{-1}$ over wavenumbers ranging from 650-4000 $cm^{-1}$ and data were processed using the Omnic software. FESEM analysis was performed on a HR-SEM electron microscope with an EDX spectrometer (JEOL JSM-6700F, Tokyo, Japan). To determine the loading content and loading efficiency, the biodegradable nanocomplexes were collected by ultracentrifugation at 30,000 rpm, 4° C. for 60 min, and the free DJ NS1 protein concentration was analyzed in the supernatant by high-performance liquid chromatography (HPLC). The carried substance loading content and loading efficiency of the nanocomplexes were determined as described in the literature and calculated from the following equations.

$$\text{loading content (\%)} = \frac{\text{total amount of the carried substance} - \text{amount of free carried substance}}{\text{weight of nanocomplex}} \times 100$$

$$\text{loading efficiency (\%)} = \frac{\text{total amount of the carried substance} - \text{amount of free carried substance}}{\text{total amount of the carried substance}} \times 100$$

7. Mice

C3H/HeN mice were obtained from National Laboratory Animal Center, Tainan facility and maintained on standard laboratory food and water in the Laboratory Animal Center of National Cheng Kung University Medical College. Their 6-week-old progeny were used for the experiments. Animal handling and procedures were reviewed and approved by the Institutional Animal Care and Use Committee (IACUC) of National Cheng Kung University, and conducted in accordance with the Guidelines for Committee of Laboratory Care and Use, National Cheng Kung University.

8. Cell Cultures

Baby hamster kidney cells (BHK-21) and C6/36 cells were cultured in Dulbecco's modified Eagles medium (DMEM) (Invitrogen) containing antibiotics and 5% or 10% fetal bovine serum (FBS). Cells were detached using 1000 U/ml trypsin and 0.5 mM EDTA. Human monocytic THP-1 cells were grown in RPMI 1640 medium (Invitrogen) containing 2 mM L-glutathione, 1 mM sodium pyruvate and supplemented with 10% FBS.

9. Virus Culture

DENV serotype 2 (strain 16681) was maintained in C6/36 cells. Briefly, monolayers of C6/36 cells were incubated with DENV at a multiplicity of infection (MOI) of 0.01 and incubated at 28° C. in 5% $CO_2$ for 5 days. The cultured medium was harvested and cell debris was removed by centrifugation at 1000×g for 10 min. The virus supernatant was collected and stored at −70° C. until use. Virus titer was determined by plaque assay using the BHK-21 cell line.

10. Mouse Immunization and Challenge

DJ NS1 proteins were encapsulated into polymer-based nanocomplexes or emulsified with an equal volume of alum solution (Thermo). The preparations were tested for endotoxin level using ToxinSensor Chromogenic LAL Endotoxin Assay Kit (GenScript). The endotoxin levels were all <1 EU/ml. C3H/HeN mice were subcutaneously injected twice (with an interval of 14 days) with 25 µg/mouse DJ NS1 proteins in polymer-based nanocomplexes or alum. Three days or 21 weeks (for long-term protection model) following the final immunization, mice were intradermally injected with medium or DENV ($2 \times 10^8$ PFU/mouse) at four sites on the upper back and sacrificed at day 3 after inoculation.

11. Antibody Titer Determination

DJ NS1 proteins were coated on 96-well plates at 0.2 mg/well in coating buffer ($NaCO_3$ 1.59 g, $NaHCO_3$ 2.93 g, pH 9.6, in 1 L dd$H_2O$) at 4° C. overnight. The plates were blocked with 1% bovine serum albumin (BSA) in PBS at 4° C. overnight, and then washed three times with 0.05% Tween 20 in PBS (PBS-T). Mouse sera were diluted serially from 1:1000 to 1:2048000. The diluted mouse sera were added into protein-coated wells, and incubated at 4° C. overnight. After washing three times, peroxidase-conjugated anti-mouse IgG or IgM was added into each well and incubated for 2 h at room temperature. After washing, ABTS (Sigma-Aldrich) was added into each well and the absorbance was measured at 405 nm.

12. Mouse Tall Bleeding Time

Bleeding time was performed with a 3-mm tail-tip transaction. Blood droplets were collected on filter paper every 30 sec. Bleeding time was recorded when the blood spot was smaller than 0.1 mm in diameter.

13. Detection of Serum MCP-1 Levels

The concentrations of serum MCP-1 were measured by a flow cytometry application with Cytometric Bead Array (CBA; BD Biosciences). Briefly, the standard mixtures were prepared by serial dilutions. Then, 50 ml of mouse sera or standards were incubated with 50 ml of prepared biotin-conjugated capture beads mixture for 1 h at room temperature. Then, 50 ml of prepared streptavidin-PE detection beads mixture were added for 1 h at room temperature. After washing twice with 1 ml of washing buffer, the beads were resuspended with 200 ml of assay buffer. The data were collected by flow cytometry and results were further analyzed by FCAP Array v3.0 Software (BD Biosciences).

14. Immunohistochemistry Staining

The skin sections were embedded in paraffin and sliced on slides. Slides were deparaffinized using xylene and gradient alcohol (100%, 95%, 85%, 70% and 50%). The sections were then incubated in 2N HCl solution for 20 min followed by treatment with 20 mg/ml proteinase K in TE buffer (50 mM Tris Base, 1 mM EDTA, and 0.5% Triton X-100, pH 8.0) for another 20 min at room temperature. The sections were incubated with 3% $H_2O_2$ in PBS for 15 min to inhibit endogenous peroxidase activity and blocked by 5% BSA in PBS-T.

The primary and secondary Abs were adequately diluted in Ab diluents (Dako Corporation). The DENV antigen was stained with polyclonal anti-DENV NS3 Abs (GeneTex) overnight at 4° C., followed by biotin-labeled donkey anti-rabbit Abs at room temperature for 1 h. The infiltrating macrophages were stained by rat anti-mouse F4/80 Abs (AbD Serotec, clone CI:A3-1) overnight at 4° C., followed by biotin-labeled donkey anti-rat Abs (Jackson ImmunoResearch Laboratories) at room temperature for 2 h. After washing with PBS-T twice, the sections were incubated with HRP-conjugated streptavidin (Dako Corporation) for 15 min at room temperature. The skin sections were developed with the AEC substrate kit (Dako Corporation) and nuclei were further stained with hematoxylin (ScyTek Laboratories) for 10 sec. The positive cells were counted in 15 regions per mouse skin field and the average numbers of positive cells were calculated by HistoQuest software (TissueGnostics).

16. Statistical Analysis

Data was expressed as the mean±SD. Multiple intergroup comparisons were assessed by one-way ANOVA, followed by post hoc Tukey's test with GraphPad Prism version 6.0. Statistical significance was set at $P<0.05$.

Example 1

Prepare a First Solution Comprising a First Electrically Charged Substance

The first solution comprised a first electrically charged substance, and the first electrically charged substance was polyglutamic acid (γ-PGA) or heparin and the first electric property was negative charge, for example. In detail, a proper amount of polyglutamic acid was added into de-ionized water and stirred by electromagnetic stirrer until the polyglutamic acid was totally dissolved. Then, the sodium in the polyglutamic acid solution was removed by membrane dialysis. The dialysis process was accomplished at 4° C. for preventing bacterial growth. After dialysis, the polyglutamic acid solution was put at −20° C. for being totally frozen. Then, the water content of the frozen polyglutamic acid solution was removed by lyophilization to obtain the crystallized powder of the polyglutamic acid. The crystallized powder of the polyglutamic acid was stored in a sterilized tube and put in a moisture-proof box. Finally, a proper amount of crystallized powder of the polyglutamic acid was taken and dissolved in the de-ionized water in a desired concentration, which was the first solution comprising the first electrically charged substance with negative charge.

However, one skilled in the art will readily recognize that the aforementioned method for preparation of the first solution is one of embodiments. After reading and understanding the descriptions of the present invention, it will be obvious to those skilled in the art that various modifications may be made and not limited to the aforementioned embodiment.

Example 2

Prepare a Mixture Solution Containing a Dengue Viral Protein and the First Solution A dengue viral protein with the same electric property as the first electrically charged substance was dissolved in the first solution to form a mixture solution with negative charge. The dengue viral protein was disclosed in the Taiwan Patent Publication No. 201210614 "Dengue vaccine, medicinal composition comprising the same, and nucleotide sequence." The dose of the dengue viral protein was 100 μg, 200 μg, or 400 μg, and it was not limited thereto.

It is noted that the aforementioned dengue viral protein can be dengue envelope protein or dengue nonstructural protein. According to an embodiment of the present invention, the dengue viral protein of SEQ ID NO: 1 is disclosed in the U.S. Patent Publication No. 20120065373 "Dengue vaccine, medicinal composition comprising the same, and nucleotide sequence", the contents of which are hereby incorporated by reference herein. The dengue viral protein comprises a nonstructural chimeric protein DJ NS1. The nonstructural chimeric protein DJ NS1 comprises N-terminal amino acid 1-270 of a dengue virus nonstructural protein (DV NS1) and C-terminal amino acid 271-352 of a Japanese encephalitis virus nonstructural protein (JEV NS1). The dengue viral protein of SEQ ID NO: 2 is a nonstructural protein DJ NS1ΔC comprising N-terminal amino acid 1-270 of the dengue virus nonstructural protein.

Example 3

Prepare a Second Solution Comprising a Second Electrically Chained Substance

A second solution comprising a second electrically charged substance was prepared, and the first electric property was opposite to the second electric property. The second electrically charged substance was chitosan or collagen, for example, and the second electric property was positive charge. In detail, the second electrically charged substance was chitosan. 5 g low-viscous chitosan was added into 495 ml de-ionized water with 5 ml glacial acetic acid and stirred by electromagnetic stirrer until the chitosan solution stays in a yellow and pellucid state. It was worth noted that $NH_2$ of the chitosan was converted to $NH_3^-$ under an acidic condition, so the chitosan was positively charged. Moreover, the acetylation degree of the chitosan influenced the ratio of the positive electric charge on the chitosan. For example, when the acetylation degree of the chitosan was 100%, the $NH_2$ of the chitosan was totally converted to $NH_3^+$; however, if the acetylation degree of the chitosan was less than 100%, there would be acetyl groups on the chitosan, and those acetyl groups would be not positively charged under an acidic condition, so the total quantity of positive charge of the chitosan would be decreased. Accordingly, more chitosan must be added into the de-ionized water with glacial acetic acid to reach the desired quantity of positive charge in the chitosan solution. Next, the glacial acetic acid in the chitosan solution was removed by membrane dialysis, and the pH of the chitosan solution was about 6.5 after dialysis. Then, the chitosan solution was filtrated by air suction filter to remove the impurity. Finally, the chitosan solution was heated and stirred at 135° C. for being concentrated until the concentration of the chitosan solution reaches 20-30 mg/ml, which was the second solution comprising the second electrically charged substance.

Similarly, one skilled in the art will readily recognize that the aforementioned method of preparation of the second solution is one of embodiments. After reading and understanding the descriptions of the present invention, it will be obvious to those skilled in the art that various modifications may be made and not limited to the aforementioned embodiment.

It is noted that the aforementioned first and second electrically charged substances can be natural macromolecules, such as heparin or polyglutamic acid, and chitosan or collagen, respectively. The aforementioned first and second electrically charged substances also can be synthetically biodegradable macromolecules.

Example 4

Form a Biodegradable Nanocomplex

Figure 4:
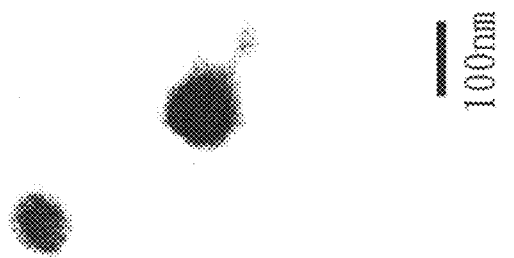
FIG. 4 is an electron microscope image of a biodegradable nanocomplex holding a dengue viral protein inside according to an embodiment of the present invention.

The mixture solution was added into the second solution to form a biodegradable nanocomplex by attraction force between the different electric properties, and the carried substance (i.e. dengue viral protein) was held in the biodegradable nanocomplex. FIG. 4 is an electron microscope image of a biodegradable nanocomplex holding a dengue viral protein inside according to an embodiment of the present invention. It is worth noted that the dengue viral protein with negative charge is mixed with the polyglutamic acid solution with negative charge to form a mixture solution first, and then the mixture solution is mixed with the chitosan solution with positive charge to form the biodegradable nanocomplex solution, in which the structure of the biodegradable nanocomplex is more stable. However, the dengue viral protein with negative charge also can be mixed with the chitosan solution with positive charge first to form a mixture solution, and then the mixture solution is mixed with the polyglutamic acid solution. Because of the biodegradability of the first and second electrically charged substances, the nanocomplex formed from the first and second electrically charged substances had biodegradability as well. The biodegradability means that the nanocomplex is decomposed, absorbed and removed easily and naturally by the human body after it enters the human body, and the carried substance held in the nanocomplex is released slowly for the sustained release. Table 4 is the particle size and the zeta potential of the biodegradable nanocomplex with and without holding the carried substance (i.e. dengue viral protein) at various charge ratio of chitan to polyglutamic acid (CS/γ-PGA). The results of the particle size and zeta potential are the average value of three biodegradable nanocomplexes.

TABLE 4

| | without holding dengue viral protien | with holding dengue viral protein CS/γ-pga = 4:1 | CS/γ-pga = 6:1 | CS/γ-pga = 8:1 |
|---|---|---|---|---|
| Size (nm) | 126.4 ± 5.1 | 124.5 ± 1.8 | 130.5 ± 2.5 | 123.1 ± 1.7 |
| Zeta potential (mV) | 83.5 ± 6.2 | 15.4 ± 0.7 | 22.9 ± 0.8 | 31.1 ± 0.7 |

Example 5

Administration with the Biodegradable Nanocomplex Holding Dengue Viral Protein Inside on a Mouse Model Mice are vaccinated with the biodegradable nanocomplex holding the dengue viral protein inside as a model compound. C3H/HeN mice were obtained from the Jackson Laboratory, and maintained on standard laboratory food and water in the Laboratory Animal Center of National Cheng Kung University Medical College in Taiwan (R.O.C.).

Housing, breeding, and experimental use of the animals were performed in strict accordance with the Experimental Animal Committee in the laboratory animal center of National Cheng Kung University. Table 5 is the results of a titer of a neutralizing antibody in the mice vaccinated by the biodegradable nanocomplex holding the dengue viral protein inside of the present invention, by the traditional Alum adjuvant, or by the traditional Ribi adjuvant.

TABLE 5

| Administration time | Antibody titer to the DJ NS1 ($\times 10^3$) | | | | | |
|---|---|---|---|---|---|---|
| | Nanocomplex (μg/mouse) | | Alum (μg/mouse) | | Ribi (μg/mouse) | |
| | 25 | 50 | 25 | 50 | 25 | 50 |
| First | ND | ND | ND | ND | ND | ND |
| Second | $2^8$ | $2^9$ | ND | ND | ND | ND |
| Third | $2^{10}$ | $2^{11}$ | $2^6$ | $2^8$ | $2^7$ | $2^8$ |

According to Table 5, after administration twice, a specific antibody response was induced by the dengue vaccine comprising the biodegradable nanocomplex of the present invention, and the mice had the antibody titer of 256000 when the dose of the biodegradable nanocomplex in the dengue vaccine is 25 μg per administration. Accordingly, the administration times of the biodegradable high-efficiency dengue vaccine in the present invention is decreased, so the biodegradable high-efficiency dengue vaccine is good for being a commercial vaccine. The ND means that the antibody titer is non-detectable. The antibody titer was measured by an ELISA standard protocol. The time of antibody response induced by the biodegradable nanocomplex was faster than that induced by the traditional Alum adjuvant and Ribi adjuvant. In detail, the traditional Alum adjuvant and Ribi adjuvant induced the specific antibody response to the dengue viral protein in the mice until the third administration. Moreover, after the third administration, the antibody titer induced by the biodegradable nanocomplex of the present invention was higher than that induced by the aforementioned Alum adjuvant and Ribi adjuvant. It is suggested that the biodegradable nanocomplex holding dengue viral protein inside enhanced the adjuvant effect in the dengue vaccine. The aforementioned Ribi adjuvant was non-toxic and non-immunity oil-in-water emulsions in Ribi adjuvant system (RAS) developed by the Ribi Immunochem Research Inc. in 1985.

In the other embodiment of the present invention, the biodegradable nanocomplex made from heparin as the first electrically charged substance and chitosan as the second electrically charged substance also induced the specific antibody response to the dengue viral protein in mice after the second administration, and the dose of the biodegradable nanocomplex in the dengue vaccine is 25 μg per administration. The organism had the antibody titer of 32000 at least after the second administration.

A pharmaceutical composition comprising the dengue vaccine comprising the aforementioned biodegradable nanocomplex is also provided, which is used for producing a vaccine or a drug for treating or preventing hemorrhagic dengue fever or dengue shock syndrome. The pharmaceutical composition comprises the aforementioned biodegradable high-efficiency dengue vaccine or an addition salts thereof with a pharmaceutically acceptable base, and at least one pharmaceutically acceptable excipient. Moreover, the pharmaceutical composition of the present invention can be administered to animals in any existing ways, i.e. oral, nasal, mucosal, topical, dermal, and parenteral administration, wherein parenteral administration is intravenous, intraperitoneal, intradermal, subcutaneous, or intramuscular administration. The pharmaceutical composition of the present invention also can be administered via the combination of the aforementioned administrations. For example, the first administration is via parenteral administration, and the second administration is via mucosal administration. In addition, the dose of the pharmaceutical composition varies depending on the species, age, weight, and status of individuals, the disease to be prevented or treated, the seriousness of the disease, the specific compound use in the pharmaceutical composition, and administration methods. One skilled in the art will readily recognize the publication content of the present invention, a proper dose can be decided by the routine experiment, and after the first administration, the organism can be decided to receive one or more additional administrations at a proper interval.

Hereinafter, there are several reasons why the present invention emphasizes "the charge ratio of the second electrically charged substance to the first electrically charged substance" and "the biodegradable nanocomplex made from the immunogenic composition has positive charge for holding the dengue viral protein inside".

Example 6

Before further discussion, it should be mentioned that, commercially available CS and γ-PGA had molecules of various molecular weights, respectively, approximately ranging from 100K to 1,000K kDa, exhibiting Boltzmann distribution of different molecular weights (unshown), which was also available at http://pslc.ws/macrog/weight-.htm. It should be noted that, the molecular weight of Boltzmann distribution increased from right to left in the figure of http://pslc.ws/macrog/weight.htm.

Moreover, as understood by a skilled person in the art, the commercially available CS and γ-PGA of different molecular weights also had different surface charges, respectively. The surface charges of various CS or γ-PGA of different molecular weights were obtained "only by measuring zeta potentials" rather than converting molecular weight.

6.1 the "Zeta Potential" of CS/γ-PGA Claimed by the Present Invention MUST BE Gotten or Measured Rather than being Mathematically Converted from its Weight Ratio Reference was made to Tables 3 and 4 according to Example 6, for clarifying that biodegradable nanocomplexes had the same "charge ratio" of CS/γ-PGA from different weight ratios of CS/γ-PGA, and not vice versa.

As shown in Table 6 of Example 6, 4 groups of the biodegradable nanocomplexes had the same "charge ratio" (for example, 4:1) of CS/γ-PGA, but they had different weight ratios due to different molecular weights of the CS and γ-PGA. According to the process of the present invention, the surface charge of the specific CS and γ-PGA was known "before mixing the carried substance, γ-PGA and CS", and all of the nanocomplexes having the same CS/γ-PGA charge ratio from different molecular weights of the CS and γ-PGA could be applied to deliver the carried substance.

TABLE 6

| | charge % (chitosan:r-pga) 4:1 | |
|---|---|---|
| | molecule weight (kDa) | wt % (chitosan:r-pga) |
| chitsan 1 (original) | 100-130K | 5.76:1 |
| chitsan 2 | 110K-150K | 4.72:1 |
| chitsan 3 | 60K-120K | 6.22:1 |
| chitsan 4 | 140K-220K | 5.85:1 |

PS. Chitsan 1 (original) refers to the one used in the present invention.

6.2 Biodegradable Nanocomplexes Having "the Same Weight Ratios" of CS/γ-PGA Contribute to Different "Charge Ratio" of CS/γ-PGA As shown in Table 7 of the Supplement Example, the nanocomplexes have different charge ratios even they have the same CS/γ-PGA weight ratio (for example, 5.76:1) due to these nanocomplexes having different molecular weights of the CS and γ-PGA.

TABLE 7

| | 5.76:1 | |
|---|---|---|
| | molecule weight (kDa) | charge % (chitosan:r-pga) |
| chitsan 1 (original) | 100-130K | 4:1 |
| chitsan 2 | 110K-150K | 3.45:1 |
| chitsan 3 | 60K-120K | 5.12:1 |
| chttsan 4 | 140K-220K | 4.45:1 |

PS. Chitsan 1 (original) refers to the one used in the present invention.

6.3 the Redundant Experiments Will be Increased More if the Zeta Potentials of the Carried Substance, the First Electrically Charged Substance and the Second Electrically Charged Substance DO NOT be Measured In prior arts, it attempted to find out the best weight ratio of CS and γ-PGA from "dozens of weight ratios of CS and γ-PGA".

As aforementioned, CS and γ-PGA respectively included various molecules of different molecular weights, and one skilled in the art tried hardly to find out the best weight ratio of CS and γ-PGA from "dozens of weight ratios of CS and γ-PGA".

However, the prior art DID NOT measure the zeta potentials of the carried substance, the first electrically charged substance and the second electrically charged substance before mixing them, the resultant nanoparticles include positively and negatively charged ones in a preferable ratio must be obtained from "redundant" experiments.

6.4 the Present Invention Makes the Biodegradable Nanocomplexes "Only in a SINGLE Test"

On the contrary with the prior art, according to the strategy of the present invention, the surface charges (i.e., zeta potentials) of the specific CS and γ-PGA are known, all of the nanocomplexes having the same CS/γ-PGA charge ratio from different molecular weights of the CS and γ-PGA could be applied to deliver the carried substance "only in single test", thereby successfully and substantially eliminating the testing numbers for finding out the best ratio of CS and γ-PGA, as shown in Table 4 of the present invention.

It should be supplemented that, the charged ratio of CS to γ-PGA in TABLE 4 of the present invention is merely as an example for delivering the DJ NS1 but is not limited thereto.

By the way, the immunogenic composition of the present invention could be applied in the field of vaccine compositions. Generally, the vaccine is preferably positively charged, so that it could improve the antigen presentation and enhance the T-cell-specific immune responses. The cationic surface charge of the CS/γ-PGA nanocomplex could enhance the antigen presentation efficiency as published on PNAS 112(2): 188-193, 2015. It was realized that the negatively charged biodegradable nanocomplexes are redundant in the vaccine composition.

Example 7

7.1 Development of DJ NS1-Encapsulated Nanocomplexes with Degradable Polymers by an Electro-Kinetic Approach The polymer-based nanocomplexes were produced using an electro-kinetic approach involving the ionic attraction of chitosan (positively-charged polymer) and γ-PGA (negatively-charged polymer), which are FDA-approved biodegradable polymers. DJ NS1 protein was introduced to form the nanocomplexes. The diameter of DJ NS1-encapsulated nanocomplexes was −280 nm with a positive surface zeta potential, +13.8 mV, by quasi-elastic light scattering (QELS) measurement. Such nanocomplexes were stable for at least six months as shown in Table 8.

TABLE 8

The particle size and zeta potential of DJ NS1-encapsulated nanocomplexes.

| | DJ NS1 | DJ NS1-encapsulated nanocomplexes | empty nanocomplexes | AuNP[b] |
|---|---|---|---|---|
| Particle size[a] (nm) | 7.4 ± 0.8 | 284.0 ± 30.8 | 268.0 ± 55.2 | 15.9 ± 0.6 |
| Zeta potential[a] (mV) | −30.2 ± 1.3 | 13.8 ± 0.5 | 30.5 ± 2.2 | −38.6 ± 2.3 |

[a]The particle size and zeta potential of 10-fold diluted nanocomplexes were measured by quasi-elastic light scattering (QELS) analyzer (632 nm He—Ne laser, 10,000:1 polarity, 5 mW) at 25° C. (n = 3)
[b]The 13-nm gold nanoparticle solution (AuNP, 10 nM) served as a measurement reference control.

Compared with empty nanocomplexes, encapsulated nanocomplexes possessed larger particle size and lower positive surface charge, likely resulting from negatively-charged DJ NS1 (Table 8). Field-emission scanning electron microscopy (FE-SEM) analysis showed the particle size was about 250 nm, as shown in FIG. 5*a*. As expected, the measured size was slightly smaller than that determined by quasielastic light scattering (QELS) analysis, since the former measures the "solid" particle diameter without the hydrodynamic layer as shown in FIGS. 5*d* and 5*e*. FIG. 5*d* was a profile of the stability of the biodegradable nanocomplexes measured by quasi-elastic light scattering (QELS) spectrometer (632 nm He—Ne laser, 10,000:1 polarity, 5 mW). FIG. 5*e* was an electrophoretic phase plot of the biodegradable nanocomplexes monitored by photon correlation spectrometer (PCL).

Energy-dispersive X-ray spectroscopy (EDX) demonstrated the existence of DJ NS1 protein (detected by sulfur content) in nanocomplexes (FIG. 5b). The composition of DJ NS1-encapsulated nanocomplexes was further analyzed by Fourier transformed infrared spectroscopy (FT-IR), as shown in FIG. 5c. Wavenumber assignments were 864 $cm^{-1}$ (—C—O—C skeletal mode), 900 $cm^{-1}$ (β-glucose, —C—O—C skeletal mode), 1071 $cm^{-1}$ (glucose), 1099 and 1152 $cm^{-1}$ (C—N vibration mode), 1260 $cm^{-1}$ (amide III, unordered), 1302 $cm^{-1}$ (amide III), 1321 $cm^{-1}$ (amide III, α helix), 1370 $cm^{-1}$ (saccharide band), 1449 $cm^{-1}$ (C—H bending in protein), 1542 $cm^{-1}$ (—$NH^{3+}$ vibration mode of chitosan), 1586 $cm^{-1}$ (—$COO^-$ vibration mode of γ-PGA), and 1647 $cm^{-1}$ (amide I, α helix). Signals at 1321, 1449 and 1647 $cm^{-1}$ derived from the characteristic vibration modes of protein structures. Those results were clear evidence for the encapsulation of DJ NS1 protein with a homogeneous distribution into nanocomplexes. The loading content and loading efficiency of DJ NS1 protein in nanocomplexes were 72% and 27%, respectively, as determined by high-performance liquid chromatography (HPLC).

7.2 Active Immunization with DJ NS1 Protein Encapsulated in Nanocomplexes Induces Higher Levels of DJ NS1-Specific Abs than DJ NS1 Combined with Alum To investigate the Ab responses induced by DJ NS1-encapsulated nanocomplexes, C3H/HeN mice were subcutaneously immunized with 25 μg/mouse of DJ NS1 protein in nanocomplexes or alum. Alum had been widely used as a standard adjuvant for human vaccines. After two rounds of immunization, the DJ NS1-specific Ab titers were determined in the mouse sera.

The mice inoculated with DJ NS1-encapsulated nanocomplexes elicited titers of $2^7$ (×$10^3$) for anti-DJ NS1 IgG and $2^4$ (×$10^3$) for anti-DJ NS1 IgM, whereas the mice inoculated with DJ NS1 plus alum elicited titers of only $2^4$ (×$10^3$) for anti-DJ NS1 IgG and $2^3$ (×$10^3$) for anti-DJ NS1 IgM. Based on these results, DJ NS1-encapsulated nanocomplexes could induce higher specific IgG and IgM titers when compared with DJ NS1 plus alum.

Alum adjuvant could provoke a strong Th2 response, whereas certain particulates such as various vesicles may induce a Th1 or Th2 response depending on their size. Therefore, the levels of DJ NS1-specific IgG2a and IgG1 Abs for Th1 and Th2 responses were determined, respectively, in mouse sera after two rounds of immunization. The results showed that DJ NS1-encapsulated nanocomplexes can induce both IgG1 and IgG2a Abs, while DJ NS1 plus alum mainly induced IgG1 Abs, as shown in FIGS. 6a and 6b. To determine the cytokine profiles, lymphocytes were collected from immunized mice and re-stimulated with 5 μg/ml of DJ NS1 for 72 h. Cytokine concentrations including IFN-γ, IL-2 and IL-4 in the culture supernatants were determined. The cytokine profiles showed higher Th1 cytokine levels (i.e., IFN-g and IL-2) in the NS1-encapsulated nanocomplexes-treated group as compared with the NS1 plus alum-treated group. Both DJ NS1-encapsulated nanocomplexes and DJ NS1 plus alum induced the Th2 cytokine, IL-4, although DJ NS1 plus alum induced higher levels than did DJ NS1-encapsulated nanocomplexes, as shown in FIG. 6c. These results indicated that DJ NS1-encapsulated nanocomplexes induce both Th1 and Th2 responses, while DJ NS1-adsorbed alum mainly induces a Th2 response.

7.3 Active Immunization with DJ NS1-Encapsulated Nanocomplexes Decreases DENV-Induced Prolonged Bleeding Time, and Reduces Viral NS3 Antigen Expression and Macrophage Infiltration at the Skin Inoculation Site Our previous study showed that anti-DJ NS1 Abs provided protective effects against DENV infection in mice. In this study, the protective effects of DJ NS1 protein were further evaluated by using nanocomplexes as adjuvant. Following immunization of mice with 25 μg/mouse of DJ NS1 protein in nanocomplexes or alum, mice were challenged with 2×$10^8$ PFU/mouse of DENV and the tail bleeding time was determined at 3 days post-infection, as shown in FIG. 7a. Results showed that the prolonged bleeding time induced by DENV was significantly reduced in the DJ NS1-encapsulated nanocomplexes group than in the DJ NS1-adsorbed alum group. Moreover, the bleeding time of mice immunized with DJ NS1-encapsulated nanocomplexes, followed by DENV challenge, was similar to that of non-infected mice, as shown in FIG. 7b.

MCP-1 is a highly expressed chemokine in DHF/DSS patients and can be presented on the surface of high endothelial venules for recruitment of monocytes. In the mouse model, MCP-1 contributes to attracting macrophages in response to DENV infection. Following, the levels of MCP-1 in mouse serum and the levels of F4/80-positive macrophages infiltrated to the dermis layer were determined. Results showed that active immunization with DJ NS1-encapsulated nanocomplexes reduced DENV-induced MCP-1 production, as shown in FIG. 8.

7.4 Active Immunization with DJ NS1-Encapsulated Nanocomplexes can Provide Long-Lasting Ab Responses and Long-Term Protection A successful dengue vaccine must achieve several criteria, one of which is to provide long-lasting immunity. In this EXAMPLE, the Ab responses in mice inoculated were compared with 25 μg of DJ NS1 protein combined with either nanocomplexes or alum. After two rounds of immunization, the DJ NS1-specific IgG and IgM titers were determined in mouse sera every week, as shown in FIG. 9a. Results showed that the Ab titers induced by DJ NS1-encapsulated nanocomplexes remained detectable till 18-19 weeks after immunization. In contrast, the Ab titers induced by DJ NS1 plus alum could be detected only up to 8 weeks after immunization, as shown in FIGS. 9b and 9c.

To determine whether active immunization with DJ NS1-encapsulated nanocomplexes can protect against the DENV-induced prolonged bleeding time, mice were challenged with 2×$10^8$ PFU/mouse of DENV at 21 weeks after immunization, and then determined the bleeding time at 3 days post-infection. The results showed that active immunization with DJ NS1-encapsulated nanocomplexes significantly reduced the DENV-induced prolonged bleeding time when compared with the DJ NS1 plus alum group, as shown in FIG. 9d. The mouse sera was also collected on 3 days post-infection to determine the DJ NS1-specific Ab titers after DENV infection.

Results showed that mice inoculated with DJ NS1-encapsulated nanocomplexes induced an anti-DJ NS1 IgG titer of $2^6$ (×$10^3$). In contrast, mice inoculated with DJ NS1 plus alum showed an anti-DJ NS1 IgG titer of only $2^4$ (×$10^3$). These results indicate that mice immunized with DJ NS1- encapsulated nanocomplexes induce higher Ab responses than mice immunized with DJ NS1 plus alum.

Example 8

Evaluation of Nanocomplex with Different Charge Distribution

A low-MW CS was obtained from the depolymerization of a commercially available CS. Given a low-MW, the polycationic CS had a good solubility at a pH value close to physiological range. CS (MW 280 kDa) with a degree of deacetylation of approximately 85% (Sigma-Aldrich, St. Louis, Mo., USA) was treated with sodium perborate tetrahydrate ($NaBO_3$, Sigma-Aldrich) to produce low-MW CS.

Sample 1

First, the zeta potential of sample of 25 μg of DJ-NS1 protein in 1 ml and aqueous γ-PGA (1 mg/ml, 1 ml, 1.6 nM, i.e. polymer 1), was measured, respectively. The difference of zeta potential (polymer1 minus carried substance) was about 10 mV. And these two solutions were premixed, followed by adding into aqueous CS (3 mg/ml, 3 ml, 32 nM, i.e. polymer 2) under magnetic stirring in the 10 mM phosphate buffer (pH=6) at 25° C., for forming the nanocomplex of Sample 1 (final zeta potential: 11.7±0.6 mV, particle size: 278.0±22.5 nm).

Sample 2

First, the zeta potential of sample of 25 μg of DJ-NS1 protein in 1 ml and aqueous γ-PGA (1 mg/ml, 1 ml, 1.6 nM, i.e. polymer 1), was measured, respectively. The difference of zeta potential (polymer1 minus carried substance) is about 10 mV. Next, added the polymer 2 (CS, 3 mg/ml, 10 μL, 0.1 nM) into the polymer 1 solution, and now the difference of zeta potential (polymer1 minus carried substance) is about 16 mV. These two solutions were premixed, followed by adding into aqueous CS (3 mg/ml, 32 nM, 3 ml, i.e. polymer 2) under magnetic stirring in the 10 mM phosphate buffer (pH=6) at 25° C., for forming the nanocomplex of Sample 2 (final zeta potential: 11.6±0.5 mV, particle size: 270.0±23.2 nm).

Sample 3

First, the zeta potential of sample of 25 μg of DJ-NS1 protein in 1 ml and aqueous γ-PGA (1 mg/ml, 1 ml, 1.6 nM, i.e. polymer 1), was measured, respectively. The difference of zeta potential (polymer1 minus carried substance) is about 10 mV. Next, added the polymer 1 (γ-PGA, 1 mg/ml, 10 μL, 0.05 nM) into the polymer 1 solution, and now the difference of zeta potential (polymer1 minus carried substance) is about 3 mV. These two solutions were premixed, followed by adding into aqueous CS (3 mg/ml, 3 ml, i.e. polymer 2) under magnetic stirring in the 10 mM phosphate buffer (pH=6) at 25° C., for forming the nanocomplex of Sample 3 (final zeta potential: 11.6±0.6 mV, particle size: 281.0±20.2 nm).

Samples 4 to 9

Samples 4 to 9 were practiced with the same method as in Samples 1 to 3 by using different kinds of the components of the compositions of the biodegradable nanocomplexes. The formulations and evaluation results of Samples 4 to 9 were listed in TABLE 9 rather than focusing or mentioning them in detail.

As shown in Table 9, the biodegradable nanocomplex formed by the first electrically charged substance, the charge-redistribution substance and the second electrically charged substance could hold the positively or negatively charged carried substance inside.

TABLE 9

| | | Samples | | | | | |
|---|---|---|---|---|---|---|---|
| | | 1 | 2 | 3 | 4 | 5 | 6 |
| Carried substance (A) | DJ NS1 (−) | 25 μg | 25 μg | 25 μg | 25 μg | 25 μg | |
| | Cytochrome c (+) | | | | | | 25 μg |
| First electrically charged substance (B) | γ-PGA (−) | 1.6 nM | 1.6 nM | 1.6 nM | | | |
| | Heparin (−) | | | | 58 nM | 58 nM | |
| | CS (+) | | | | | | 107 nM |
| | PEI (+) | | | | | | |
| Charge-redistribution substance (C) | CS (+) | | 0.1 nM | | 0.1 nM | | 0.1 nM |
| | γ-PGA (−) | | | 0.05 nM | | 0.05 nM | |
| Second electrically charged substance (D) | CS(+) | 32 nM | 32 nM | 32 nM | | | |
| | PEI(+) | | | | 360 nM | 360 nM | |
| | γ-PGA (−) | | | | | | 0.17 nM |
| | Heparin (−) | | | | | | |
| zeta potential I (mV) [B-A] | | 10 | 10 | 10 | 11 | 11 | 14 |
| zeta potential II (mV) of [C-zeta potential I] | | N.D. | 16 | 3 | 19 | 14 | 21 |
| Biodegradable nanocomplex | Averaged diameter (nm) | 278.0 ± 22.5 | 270.0 ± 23.2 | 281.0 ± 20.2 | 385.0 ± 30.1 | 279.0 ± 18.5 | 328.0 ± 22.5 |
| | zeta potential (mV) | 11.7 ± 0.6 | 11.6 ± 0.5 | 11.6 ± 0.6 | 25.1 ± 0.9 | 21.6 ± 0.8 | 38.6 ± 0.5 |
| | QELS | V | V | V | V | V | V |

| | | Samples | | | | |
|---|---|---|---|---|---|---|
| | | 7 | 8 | 9 | 10 | 11 |
| Carried substance (A) | DJ NS1 (−) | | | | 25 μg | 25 μg |
| | Cytochrome c (+) | 25 μg | 25 μg | 25 μg | | |
| First electrically charged substance (B) | γ-PGA (−) | | | | 1.6 nM | 1.6 nM |
| | Heparin (−) | | | | | |
| | CS (+) | 3.6 nM | | | | |
| | PEI (+) | | 1200 nM | 1200 nM | | |

TABLE 9-continued

| | | | | | | |
|---|---|---|---|---|---|---|
| Charge-redistribution substance (C) | CS (+) | | 0.1 nM | | 1.0 nM | 10 nM |
| | γ-PGA (−) | 0.05 nM | | 0.05 nM | | |
| Second electrically charged substance (D) | CS(+) | | | | 32 nM | 32 nM |
| | PEI(+) | | | | | |
| | γ-PGA (−) | 50 nM | | | | |
| | Heparin (−) | | 58 nM | 58 nM | | |
| zeta potential I (mV) [B-A] | | 10 | 14 | 14 | 10 | 10 |
| zeta potential II (mV) of [C-zeta potential I] | | 17 | 16 | 14 | 16 | 16 |
| Biodegradable nanocomplex | Averaged diameter (nm) | 305.0 ± 28.3 | 252.0 ± 21.8 | 290.0 ± 30.1 | 312 ± 28.5 | 270 ± 27.4 |
| | zeta potential (mV) | 29.7 ± 0.6 | 20.6 ± 0.5 | 22.0 ± 0.5 | 14.8 ± 0.7 | 25.5 ± 0.6 |
| | QELS | V | V | V | V | V |

Reference was made to FIGS. 10a and 10b according to Samples 1, 2, 3, 10 and 11 of Example 8. Nonuniformly (or spatially inhomogeneous) charge distribution could be imaged by the STM (Scanning Tunneling Microscopy) via the point-by-point collection of a large number of individual charge collection efficiency values. Charge distribution images of FIGS. 10a and 10b were produced by recording an electric current during a two-dimensional scan of the fabricated nanocomplex. The experiments were performed with a home-made low temperature STM, which is capable of cooling the STM and the sample down to 20 K. The STM and sample preparation station are housed in a ultra-high vacuum chamber that maintains a basal pressure of $5 \times 10^{-11}$ torr. STM imaging and current-voltage measurements used commercially available Pt—Ir probes (Materials Analytic Services, Raleigh, N.C.). During obtaining the charge distribution of nanocomplex, the tip is scanned in constant-current mode according to the tunneling setpoint conditions (0.1 nA tunneling current and −1.2 V sample bias) until it reaches the indicated point for taking current-voltage measurements. At these predetermined points, the feedback of the tip position is held constant, and the sample bias is varied while the tunneling current is recorded. In this case, the threshold of the single detection for current is 10 pA when the same state at the surface is detected in the entire current range.

FIGS. 10a and 10b showed images of molecular distributions (the images at the top row), the positively charge distributions (the images at the middle row) and the combined distributions (the images at the bottom row) of the nanocomplexes of Samples 1, 2, 3, 10 and 11 of Example 8 according to some embodiments of the present invention. FIG. 11 showed a cross-sectional diagram of the nanocomplex of Sample 2 according to an embodiment of the present invention.

As shown in FIGS. 10a, 10b and 11, the nanocomplex 110 of Sample 2 had a nonuniformally and positively charge distribution 111 along a radial direction 113 thereof, the nonuniformally and positively charge distribution 111 of the nanocomplex of Sample 2 comprised a first electrically charged portion, 111a a second electrically charged portion 111b surrounding the first electrically charged portion 111a, and a third electrically charged portion 111c surrounding the second electrically charged portion 111b. The first electrically charged portion 111a had a first volume charge density being substantially neutral (being blank in the central region of the nanocomplex of Sample 2 at the middle row of FIGS. 10a and 10b). The third electrically charged portion 111c includes an outermost surface 115 of the nanocomplex 110. In an example, the third electrically charged portion 111c has a third volume charge density (exhibiting a darker green color near the outermost surface of the nanocomplex of Sample 2 at the middle row of FIGS. 10a and 10b) more than a second volume charge density (exhibiting a lighter green color between the outermost surface and the central region of the nanocomplex of Sample 2 at the middle row of FIGS. 10a and 10b) of the second electrically charged portion 111b. In other examples, the third electrically charged portion 111c has a third volume charge density being approximately zero (i.e. the outermost surface of the nanocomplex of Sample 3 at the middle row of FIG. 10a) or less than a second volume.

Reference was made to FIGS. 12a to 12d, which showed relative levels (mean fluorescence intensity; MFI) of antibodies to MHC class I (FIGS. 12a and 12c) and MHC class II (FIGS. 12b and 12d) of mice administrated with the nanocomplexes of Samples 1 to 3 (FIGS. 12a and 12b) and Samples 2, 10 and 11 (FIGS. 12c and 12d) of Example 8 according to embodiments of the present invention.

As shown in FIGS. 12a to 12d, the nanocomplexes of Samples 2 and 10 had a higher antibody titer and higher levels of antibodies to MHC class I and MHC class II, exhibiting an better enhancement of CD8(+) T-cell response than the nanocomplexes of Samples 1, 3 and 11.

The present invention developed a polymeric particle-based adjuvant to actively immunize mice with DJ NS1 protein and to evaluate its protective effects in a DENV-infected mouse model. After two rounds of immunization, a superior Ab response induced by DJ NS1-encapsulated nanocomplexes was observed, as compared to DJ NS1 with alum. The detailed mechanisms of how DJ NS1-encapsulated nanocomplexes induce higher and long-lasting Ab titers were, however, still unclear. It has been reported that nanoparticle sizes between 200 to 600 nm are efficiently taken up by APCs. Phagocytosis occurs more efficiently if vesicles are positively charged and spherical or cylindrical in shape compared with negatively charged or disk-shaped particles. The nanoparticles used in the present invention were positively charged with a spherical shape and a diameter of approximately 280 nm.

The superior adjuvant properties of nanocomplexes over alum were clearly evident from our present study. The underlying mechanisms are not certain, but likely involve a depot effect resulting from the particulate DJ NS1 nanocomplexes at the skin inoculation site. For example, liposomes as adjuvant can form an antigen depot at the site of injection and induce immunological recall responses. In contrast, alum has been reported to fail to sustain antigen availability in draining lymph nodes and likely does not contribute to an antigen depot effect in its adjuvant activity.

Further studies are required to validate this and to determine the levels and locations of DJ NS1-encapsulated nanocomplexes processed by antigen-presenting cells, such as macrophages and DCs.

A requirement of a dengue vaccine is that the immunity elicited by the vaccine should provide long-term protection. Therefore, the levels of NS1-specific Abs in mouse sera were determined every week after immunization. It was found that the Ab titers induced by DJ NS1-encapsulated nanocomplexes remained detectable till 18-19 weeks, whereas the Ab titers induced by DJ NS1 plus alum could be detected only up to 8 weeks after immunization. Moreover, at 21 weeks when the serum Ab titer was no longer detectable, mice inoculated with DJ NS1-encapsulated nanocomplexes produced anti-DJ NS1 IgG titers of $2^6$ ($\times 10^3$) at 3 days post-infection. These data suggest that DJ NS1-encapsulated nanocomplexes can induce effective Ab responses and provide long-term protection in this DENV-infected mouse model.

Besides the efficient Ab responses, the question as to whether DJ NS1-encapsulated nanocomplexes can induce a $CD8^+$ T cell response is of interest for further investigation. In a previous study examining dengue-specific T cells from 18 dengue fever patients and 22 DHF patients, it was found that $CD8^+$ T cells mainly recognized the NS3 and NS5 proteins. However, two human $CD8^+$ T cell epitopes have been identified in the DENV4 NS1 protein. After immunization of mice with these epitope-containing peptides, DENV4 specific $CD8^+$ T cells were activated. It also remains to be determined whether the DJ NS1-encapsulated nanocomplexes can induce cross-presentation of exogenous antigen by DCs. A previous study using γ-PGA as adjuvant showed enhanced endoplasmic reticulum (ER)-endosome fusion and translocation of the confined ovalbumin antigens from the fused ER-endosome complex to the cytosol via ER-translocon sec61. Subsequently, the released antigens were degraded by cytoplasmic proteasomes and transported to the ER via TAP, followed by presentation of the antigen-MHC class I complex on the cell surface.

Previous studies showed that macrophages produce different patterns of cytokines and direct the immune response towards a Th1 or Th2 phenotype by responding to the endocytosis of large or small lipid vesicles[43]. Recent reports demonstrated that particle-based adjuvants can facilitate antigen cross-presentation to activate $CD8^+$ T cells. However, it still remains unclear as to whether nanocomplexes as adjuvant will induce a Th1, Th2, or mixed Th1/Th2 response. The DJ NS1-specific IgG2a and IgG1 Abs were determined for Th1 and Th2 responses, respectively, in mouse sera. The results showed that DJ NS1-encapsulated nanocomplexes can induce both Th1/Th2 responses, while DJ NS1 plus alum mainly induced a Th2 response. A previous study indicated that chitosan could enhance antigen-specific splenic $CD4^+$ T cell proliferation and induce a mixed Th1/Th2 response in mice. However, g-PGA-stimulated DCs favored the polarization of naïve $CD4^+$ T cells towards a Th1 phenotype. The cytokine patterns were further confirmed in mouse sera showing higher Th1 cytokine levels induced by DJ NS1-encapsulated nanocomplexes as compared with DJ NS1 plus alum. Conversely, Th2 cytokine levels were lower in the DJ NS1-encapsulated nanocomplexes group than in the DJ NS1 plus alum-treated group. In summary with DJ NS1 as antigen, nanocomplexes as adjuvant induce both Th1 and Th2 responses, but the detailed mechanisms need to be further investigated.

Several dengue vaccine candidates are in clinical trials, mostly chimeric live vaccines and live attenuated vaccines. Other candidates like subunit vaccines (envelope and NS1 proteins), whole inactive virus vaccines, and DNA vaccines are also under development. Increasing interest has focused on the NS1 as a candidate for therapeutic strategies including vaccine development. In addition to targeting cell-surface NS1 to trigger complement-mediated lysis of DENV-infected cells, a recent study showed that NS1 may trigger endothelial permeability and vascular leakage, suggesting that NS1 may be a new potential target for dengue therapeutics and vaccines. Immunization of mice with NS1 from DENV1 to DENV4 provided protection against DENV challenge. The contribution of NS1 to vascular leakage was further supported by the finding that NS1 activates cells via TLR4 and, moreover, disrupts endothelial cell monolayer integrity. Meanwhile, another study showed that NS1 may also activate cells via TLR2 and TLR6.

Ensuring cross-protection against the four different serotypes of DENV is an important issue for dengue vaccine development. Whether NS1-encapsulated polymer-based nanocomplexes can provide serotypic cross-protection needs to be determined. Besides the C-terminal region of NS1, another group found that a.a. 116-119 also showed cross-reactivity to endothelial cell autoantigen LYRIC. Therefore, additional cross-reactive regions of NS1 may also need to be considered for their potential harmful effects in NS1-based vaccine development.

In conclusion, the present study shows that active immunization with DJ NS1-encapsulated nanocomplexes can induce effective immune responses and provide protection against DENV infection. Importantly, DJ NS1-encapsulated nanocomplexes provide long-term protection in the mouse model. As compared with alum as an adjuvant, DJ NS1-encapsulated nanocomplexes possess at least three advantages: 1) inducing higher Ab titers; 2) inducing long-lasting Ab titers; and 3) inducing balanced Th1/Th2 responses. A safe and efficient vaccine against DENV should ideally focus on inducing both T cell and antibody responses. Alum is the most common adjuvant used in approved vaccines due to its safety profile and ability to enhance protective humoral immune responses. However, alum mainly stimulates a Th2 response which makes it unsuitable for certain vaccines. Therefore, DJ NS1-encapsulated nanocomplexes can induce a mixed Th1/Th2 response.

Although the present invention has been described in considerable detail with reference to certain embodiments thereof, other embodiments are possible. It is necessarily supplemented that, specific dengue viral protein, specific components, specific manufacturing process, specific experimental animals, specific analysis methods or specific apparatuses are employed as exemplary embodiments for clarifying the biodegradable nanocomplex and the method for making the same of the present invention. However, as is understood by a person skilled in the art, other proteins, other components, other manufacturing process, other experimental animals, other analysis methods or other apparatuses can be also employed in the biodegradable nanocomplex and the method for making the same of the present invention, rather than being limited thereto.

According to the above description, in comparison with the traditional technique, the immunogenic composition, the method for making a biodegradable nanocomplex using the immunogenic composition, and the vaccine composition comprising the biodegradable nanocomplex according to the present invention has the advantages as following:

1. The biodegradable nanocomplex of the present invention can induce a specific antibody response to the dengue viral protein in mice after administration twice.

In comparison with the Alum adjuvant and Ribi adjuvant used in the traditional dengue vaccine of the prior art, the administration times of the biodegradable high-efficiency dengue vaccine in the present invention is decreased to further reduce the administration cost, so the biodegradable nanocomplex is good for being a commercial vaccine.
2. After administration with the vaccine composition of the present invention twice, the organism has the antibody titer of 32000 at least. In comparison with the prior art, the vaccine composition of the present invention substantially increases the antibody production to induce the immune response efficiently for enhancing the protection effect of the vaccine composition.
3. The biodegradable nanocomplex of the vaccine composition of the present invention is made from the mixture of the biodegradable polyglutamic acid (or heparin) and chitosan to hold the dengue viral protein inside. Accordingly, the dengue vaccine is decomposed, absorbed and removed easily and naturally by the human body after it enters the human body. It resolves the unsafe problems resulting from the heavy metal of the Alum adjuvant, and the dengue viral protein held in the nanocomplex is released slowly for the sustained release.

According to the embodiments of the present invention, the aforementioned immunogenic composition, the method for making a biodegradable nanocomplex using the immunogenic composition, and the vaccine composition comprising the biodegradable nanocomplex, a desired biodegradable nanocomplex with the adjustable zeta potential and the desired particle size can be easily produced, for saving the testing numbers, obtaining the biodegradable nanocomplex with more uniform diameter and less standard deviation, and providing better administration effect to an organism.

Although the present invention has been described in considerable detail with reference to certain embodiments thereof, other embodiments are possible. Therefore, the spirit and scope of the appended claims should not be limited to the description of the embodiments contained herein.

What is claimed is:

1. A biodegradable nanocomplex, comprising: a first electrically charged substance, a charge-redistribution substance, a second electrically charged substance, and a carried substance, wherein the carried substance is held inside the biodegradable nanocomplex, wherein the biodegradable nanocomplex has a nonuniform positive charge distribution along a radial direction thereof, and the nonuniform positive charge distribution comprises: a first electrically charged portion having a first volume charge density; a second electrically charged portion surrounding the first electrically charged portion; and a third electrically charged portion surrounding the second electrically charged portion, wherein the third electrically charged portion comprises an outermost surface of the biodegradable nanocomplex, wherein the second electrically charged portion has a positive charge distribution with a second volume charge density, and the third electrically charged portion has a positive charge distribution with a third volume charge density, wherein the second volume charge density is different from the third volume charge density.

2. The biodegradable nanocomplex of claim 1, wherein the carried substance and first electrically charged substance are negatively charged.

3. The biodegradable nanocomplex of claim 2, wherein the second electrically charged substance is positively charged.

4. The biodegradable nanocomplex of claim 3, wherein the charge-redistribution substance is negatively charged or positively charged.

5. The biodegradable nanocomplex of claim 1, wherein the carried substance and the first electrically charged substance are positively charged.

6. The biodegradable nanocomplex of claim 5, wherein the second electrically charged substance is negatively charged.

7. The biodegradable nanocomplex of claim 6, wherein the charge-redistribution substance is negatively charged or positively charged.

8. The biodegradable nanocomplex of claim 1, wherein the first electrically charged substance, the charge-redistribution substance and/or the second electrically charged substance are respectively selected from the group consisting of chitosan (CS), gelatin, cationic cyclodextrin, cationic dextran, poly(L-lysine), polyethylenimine (PEI) and polyamidoamine when the first electrically charged substance, the charge-redistribution substance and/or the second electrically charged substance are positively charged.

9. The biodegradable nanocomplex of claim 1, wherein the first electrically charged substance and/or the charge-redistribution substance are respectively selected from the group consisting of γ-polyglutamic acid (γ-PGA) and heparin when the first electrically charged substance and/or the charge redistribution substance are negatively charged.

10. The biodegradable nanocomplex of claim 1, wherein a molar ratio of the charge-redistribution substance to the first electrically charged substance is 0.05 to 1.00.

* * * * *